US012599404B2

(12) United States Patent
Garai

(10) Patent No.: US 12,599,404 B2
(45) **Date of Patent: *Apr. 14, 2026**

(54) DISPOSABLE MEDICAL DEVICE INTRODUCTION SYSTEM

(71) Applicant: MEDTRONIC MINIMED, INC., Northridge, CA (US)

(72) Inventor: Ellis Garai, Woodland Hills, CA (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/350,717

(22) Filed: Jul. 11, 2023

(65) Prior Publication Data

US 2023/0346428 A1 Nov. 2, 2023

Related U.S. Application Data

(63) Continuation of application No. 17/072,867, filed on Oct. 16, 2020, now Pat. No. 11,737,783.

(51) Int. Cl.
*A61B 17/34* (2006.01)
*A61B 5/145* (2006.01)
(Continued)

(52) U.S. Cl.
CPC ...... *A61B 17/3468* (2013.01); *A61B 5/14503* (2013.01); *A61B 5/14532* (2013.01); *A61B 2560/063* (2013.01); *A61M 5/14276* (2013.01); *A61M 2005/1585* (2013.01); *A61M 2039/0205* (2013.01)

(58) Field of Classification Search
CPC .......... A61B 2560/063; A61B 17/3468; A61B 5/14503; A61B 5/14532; A61B 2562/242; A61M 2005/1585; A61M 5/14276; A61M 2039/0205; A61M 5/142; A61M 2205/3303; A61M 5/158; A61M 2005/1586; A61M 2005/1587; A61M 2005/14252; A61M 2005/1426; A61M 2005/14256; A61M 2005/14284; (Continued)

(56) References Cited

U.S. PATENT DOCUMENTS 4,562,751 A 1/1986 Nason et al.
4,678,408 A 7/1987 Nason et al.
(Continued)

*Primary Examiner* — Michael J Tsai
*Assistant Examiner* — Kathleen Paige Farrell
(74) *Attorney, Agent, or Firm* — Fortem IP LLP

(57) ABSTRACT

A disposable medical introduction system including a medical device and a disposable inserter. The disposable inserter includes a carrier to receive the medical device. The carrier includes at least one annular projection. The disposable inserter includes a retractor received within the at least one annular projection and movable relative to the at least one annular projection. The retractor has at least one retaining arm. The disposable inserter includes a needle cartridge coupled to the retractor that includes an insertion needle. The at least one retaining arm cooperates with the needle cartridge to maintain the insertion needle in a first, extended state. A movement of the retractor relative to the at least one annular projection releases the at least one retaining arm to move the insertion needle from the first, extended state to a second, retracted state.

20 Claims, 17 Drawing Sheets

(51) Int. Cl.
  *A61M 5/142* (2006.01)
  *A61M 5/158* (2006.01)
  *A61M 39/02* (2006.01)

(58) Field of Classification Search
  CPC .. A61M 2039/0232; A61M 2005/1583; A61M 2005/1581; A61M 5/14248
  See application file for complete search history.

(56) References Cited

U.S. PATENT DOCUMENTS

| | | | |
|---|---|---|---|
| 4,685,903 A | 8/1987 | Cable et al. | |
| 4,755,173 A | 7/1988 | Konopka et al. | |
| 5,080,653 A | 1/1992 | Voss et al. | |
| 5,097,122 A | 3/1992 | Colman et al. | |
| 5,312,364 A * | 5/1994 | Jacobs | A61B 17/3472 |
| | | | 604/174 |
| 5,391,250 A | 2/1995 | Cheney et al. | |
| 5,485,408 A | 1/1996 | Blomquist | |
| 5,505,709 A | 4/1996 | Funderburk et al. | |
| 5,522,803 A | 6/1996 | Teissen-Simony | |
| 5,665,065 A | 9/1997 | Colman et al. | |
| 5,800,420 A | 9/1998 | Gross et al. | |
| 5,807,375 A | 9/1998 | Gross et al. | |
| 5,925,021 A | 7/1999 | Castellano et al. | |
| 5,954,643 A | 9/1999 | Vanantwerp et al. | |
| 6,017,328 A | 1/2000 | Fischell et al. | |
| 6,186,982 B1 | 2/2001 | Gross et al. | |
| 6,246,992 B1 | 6/2001 | Brown | |
| 6,248,067 B1 | 6/2001 | Causey et al. | |
| 6,248,093 B1 | 6/2001 | Moberg | |
| 6,355,021 B1 | 3/2002 | Nielsen et al. | |
| 6,379,301 B1 | 4/2002 | Worthington et al. | |
| 6,485,465 B2 | 11/2002 | Moberg et al. | |
| 6,544,212 B2 | 4/2003 | Galley et al. | |
| 6,554,798 B1 | 4/2003 | Mann et al. | |
| 6,558,351 B1 | 5/2003 | Steil et al. | |
| 6,591,876 B2 | 7/2003 | Safabash | |
| 6,641,533 B2 | 11/2003 | Causey et al. | |
| 6,659,980 B2 | 12/2003 | Moberg et al. | |
| 6,736,797 B1 | 5/2004 | Larsen et al. | |
| 6,749,587 B2 | 6/2004 | Flaherty | |
| 6,752,787 B1 | 6/2004 | Causey et al. | |
| 6,766,183 B2 | 7/2004 | Walsh et al. | |
| 6,801,420 B2 | 10/2004 | Talbot et al. | |
| 6,804,544 B2 | 10/2004 | Van Antwerp et al. | |
| 6,817,990 B2 | 11/2004 | Yap et al. | |
| 6,892,085 B2 | 5/2005 | McIvor et al. | |
| 6,932,584 B2 | 8/2005 | Gray et al. | |
| 7,003,336 B2 | 2/2006 | Holker et al. | |
| 7,029,444 B2 | 4/2006 | Shin et al. | |
| 7,066,909 B1 | 6/2006 | Peter et al. | |
| 7,137,964 B2 | 11/2006 | Flaherty | |
| 7,303,549 B2 | 12/2007 | Flaherty et al. | |
| 7,399,277 B2 | 7/2008 | Saidara et al. | |
| 7,442,186 B2 | 10/2008 | Blomquist | |
| 7,468,033 B2 | 12/2008 | Van et al. | |
| 7,602,310 B2 | 10/2009 | Mann et al. | |
| 7,621,893 B2 | 11/2009 | Moberg et al. | |
| 7,647,237 B2 | 1/2010 | Malave et al. | |
| 7,699,807 B2 | 4/2010 | Faust et al. | |
| 7,727,148 B2 | 6/2010 | Talbot et al. | |
| 7,785,313 B2 | 8/2010 | Mastrototaro | |
| 7,806,886 B2 | 10/2010 | Kanderian et al. | |
| 7,819,843 B2 | 10/2010 | Mann et al. | |
| 7,828,764 B2 | 11/2010 | Moberg et al. | |
| 7,879,010 B2 | 2/2011 | Hunn et al. | |
| 7,890,295 B2 | 2/2011 | Shin et al. | |
| 7,892,206 B2 | 2/2011 | Moberg et al. | |
| 7,892,748 B2 | 2/2011 | Norrild et al. | |
| 7,901,394 B2 | 3/2011 | Ireland et al. | |
| 7,905,868 B2 | 3/2011 | Moberg et al. | |
| 7,942,844 B2 | 5/2011 | Moberg et al. | |
| 7,946,985 B2 | 5/2011 | Mastrototaro et al. | |
| 7,955,305 B2 | 6/2011 | Moberg et al. | |
| 7,963,954 B2 | 6/2011 | Kavazov | |
| 7,977,112 B2 | 7/2011 | Burke et al. | |
| 7,979,259 B2 | 7/2011 | Brown | |
| 7,985,330 B2 | 7/2011 | Wang et al. | |
| 8,024,201 B2 | 9/2011 | Brown | |
| 8,100,852 B2 | 1/2012 | Moberg et al. | |
| 8,114,268 B2 | 2/2012 | Wang et al. | |
| 8,114,269 B2 | 2/2012 | Cooper et al. | |
| 8,137,314 B2 | 3/2012 | Mounce et al. | |
| 8,181,849 B2 | 5/2012 | Bazargan et al. | |
| 8,182,462 B2 | 5/2012 | Istoc et al. | |
| 8,192,395 B2 | 6/2012 | Estes et al. | |
| 8,195,265 B2 | 6/2012 | Goode et al. | |
| 8,202,250 B2 | 6/2012 | Stutz | |
| 8,207,859 B2 | 6/2012 | Enegren et al. | |
| 8,226,615 B2 | 7/2012 | Bikovsky | |
| 8,257,259 B2 | 9/2012 | Brauker et al. | |
| 8,267,921 B2 | 9/2012 | Yodfat et al. | |
| 8,275,437 B2 | 9/2012 | Brauker et al. | |
| 8,277,415 B2 | 10/2012 | Mounce et al. | |
| 8,292,849 B2 | 10/2012 | Bobroff et al. | |
| 8,298,172 B2 | 10/2012 | Nielsen et al. | |
| 8,303,572 B2 | 11/2012 | Adair et al. | |
| 8,305,580 B2 | 11/2012 | Aasmul | |
| 8,308,679 B2 | 11/2012 | Hanson et al. | |
| 8,313,433 B2 | 11/2012 | Cohen et al. | |
| 8,318,443 B2 | 11/2012 | Norrild et al. | |
| 8,323,250 B2 | 12/2012 | Chong et al. | |
| 8,343,092 B2 | 1/2013 | Rush et al. | |
| 8,352,011 B2 | 1/2013 | Van Antwerp et al. | |
| 8,353,829 B2 | 1/2013 | Say et al. | |
| 9,295,786 B2 | 3/2016 | Gottlieb et al. | |
| 10,413,183 B2 | 9/2019 | Antonio et al. | |
| 2007/0123819 A1 | 5/2007 | Mernoe et al. | |
| 2008/0269687 A1 | 10/2008 | Chong et al. | |
| 2009/0299290 A1 | 12/2009 | Moberg | |
| 2009/0299301 A1 | 12/2009 | Gottlieb et al. | |
| 2010/0160861 A1 | 6/2010 | Causey et al. | |
| 2017/0290546 A1 * | 10/2017 | Antonio et al. | A61B 5/14865 |
| 2020/0289748 A1 * | 9/2020 | Lanigan et al. | |
| | | | A61M 2005/1585 |
| 2021/0378560 A1 | 12/2021 | Antonio et al. | |
| 2022/0080116 A1 * | 3/2022 | Kobayashi | A61M 5/14248 |
| 2022/0117627 A1 | 4/2022 | Garai | |

* cited by examiner

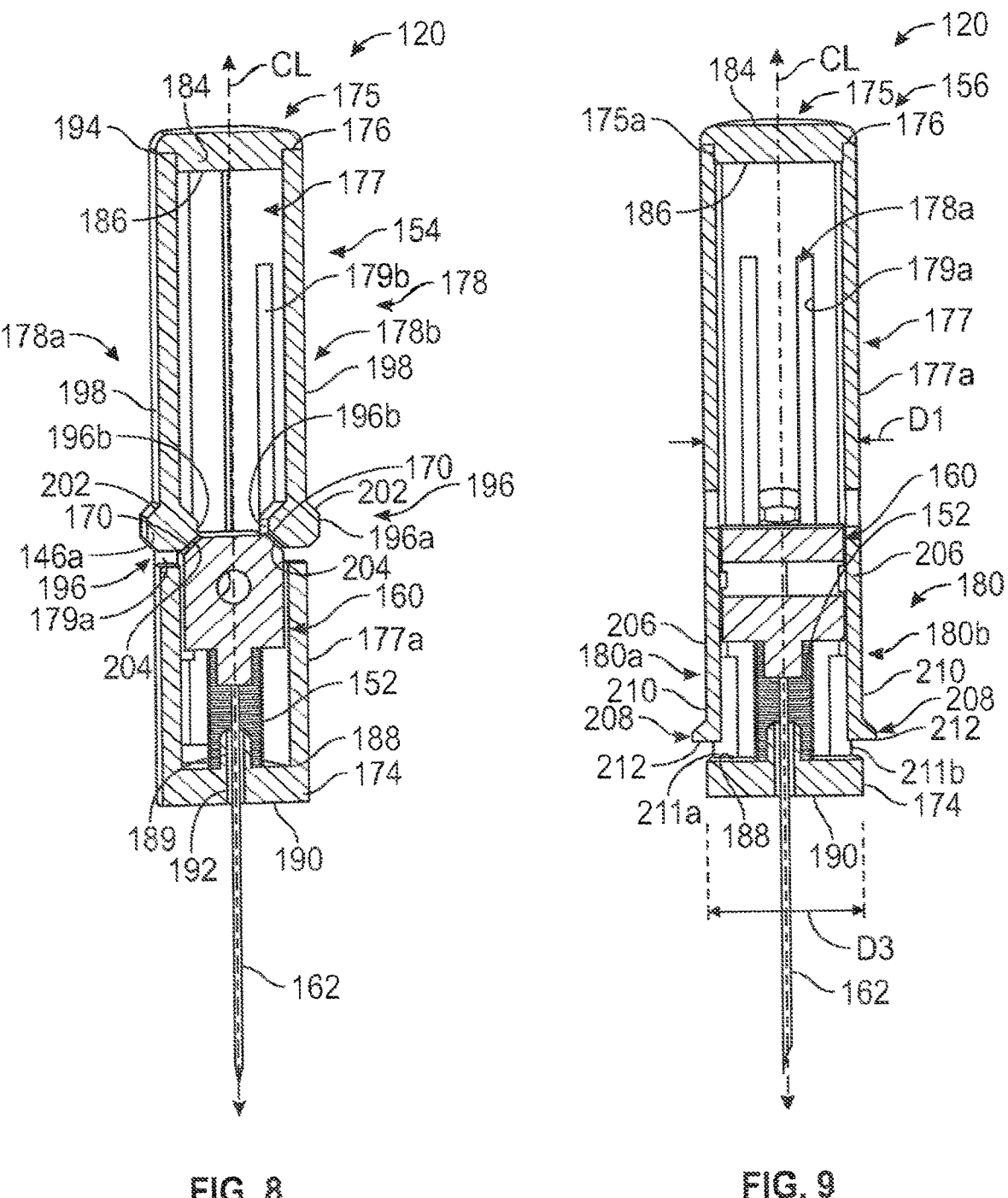
FIG. 8                    FIG. 9

DISPOSABLE MEDICAL DEVICE INTRODUCTION SYSTEM

CROSS-REFERENCE TO RELATED APPLICATIONS

This application is a continuation of U.S. application Ser. No. 17/072,867, filed Oct. 16, 2020, which is incorporated herein by reference in its entirety.

TECHNICAL FIELD

The present technology is generally related to medical devices, such as a disposable medical device introduction system for use with a medical device associated with a user, such as a physiological characteristic sensor or an infusion unit. More particularly, embodiments of the subject matter relate to a disposable medical device introduction system for a physiological characteristic sensor or an infusion unit, and a disposable inserter for coupling the physiological characteristic sensor or the infusion unit to a user.

BACKGROUND

Sensors may be employed in the treatment of or monitoring of various medical conditions. Thin film electrochemical sensors are used to test analyte levels in patients or users. More specifically, thin film sensors have been designed for use in obtaining an indication of blood glucose (BG) levels and monitoring BG levels in a diabetic user, with the distal segment portion of the sensor positioned subcutaneously in direct contact with extracellular fluid. Such readings can be especially useful in adjusting a treatment regimen which typically includes regular administration of insulin to the user. A glucose sensor of the type described above may be packaged and sold as a product, such as a continuous glucose monitor, which is adhered to the patient during use via an adhesive skin patch.

In addition, certain diseases or conditions may be treated, according to modern medical techniques, by delivering a medication or other substance to the body of a user, either in a continuous manner or at particular times or time intervals within an overall time period. For example, diabetes is commonly treated by delivering defined amounts of insulin to the user at appropriate times. Some common modes of providing insulin therapy to a user include delivery of insulin through manually operated syringes and insulin pens. Other modern systems employ programmable fluid infusion devices (e.g., insulin pumps) to deliver controlled amounts of insulin to a user. In certain instances, these fluid infusion devices require an insertion set, such as an infusion set that includes an infusion unit, to be coupled to the body of a user for the delivery of the insulin. Generally, the infusion set is coupled to the fluid infusion device via hollow tubing, which provides a fluid flow path from the fluid infusion device to the user via the infusion unit. Typically, the infusion unit requires a portion of a cannula, for example, to be inserted under the skin of the user to deliver the controlled amounts of insulin from the fluid infusion device to the user via the infusion unit.

In order to insert the glucose sensor into the user or to insert the cannula into the user, an inserter may be used, which includes a needle to puncture the skin of the user at the same time the glucose sensor or the cannula is introduced. As the inserter employs the use of a needle, the inserter is unable to be conveniently disposed of, and rather, must be disposed of in a biohazard and/or sharps container or shipped to a medical supplier for proper disposal.

Accordingly, it is desirable to provide a disposable medical device introduction system, which includes a disposable inserter for coupling a physiological characteristic sensor, such as a continuous glucose monitor, or an infusion unit, to an anatomy of a user. Furthermore, other desirable features and characteristics will become apparent from the subsequent detailed description and the appended claims, taken in conjunction with the accompanying drawings and the foregoing technical field and background.

BRIEF SUMMARY

The subject matter of this disclosure generally relates to a disposable medical device introduction system that includes a disposable inserter for coupling a medical device, such as a physiological characteristic sensor, for example, a continuous glucose sensor, or an infusion unit, to a user.

According to various embodiments, provided is a disposable inserter for a medical device. The disposable inserter includes a carrier to receive the medical device. The carrier includes at least one annular projection. The disposable inserter includes a retractor received within the at least one annular projection and movable relative to the at least one annular projection. The retractor has at least one retaining arm. The disposable inserter includes a needle cartridge coupled to the retractor that includes an insertion needle. The at least one retaining arm cooperates with the needle cartridge to maintain the insertion needle in a first, extended state. A movement of the retractor relative to the at least one annular projection releases the at least one retaining arm to move the insertion needle from the first, extended state to a second, retracted state.

Also provided according to various embodiments is a disposable medical device introduction system. The disposable medical device introduction system includes a medical device, and a disposable inserter. The disposable inserter includes a plunger defining an access opening enclosed by a removable access cover, and a carrier to receive the medical device. The carrier includes at least one annular projection, and the carrier is movable relative to the plunger. The disposable inserter includes a retractor received within the at least one annular projection and movable relative to the at least one annular projection. The retractor has at least one retaining arm. The disposable inserter includes a needle cartridge coupled to the retractor that includes an insertion needle. The at least one retaining arm cooperates with the needle cartridge to maintain the insertion needle in a first, extended state, and a movement of the retractor relative to the at least one annular projection releases the at least one retaining arm to move the insertion needle from the first, extended state to a second, retracted state. The needle cartridge is removable through the access opening.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures.

FIG. 8 is a cross-sectional view of the needle cartridge of FIG. 5, taken along line 8-8 of FIG. 5;

FIG. 9 is a cross-sectional view of the needle cartridge of FIG. 5, taken along line 9-9 of FIG. 5;

DETAILED DESCRIPTION

Figure 1:
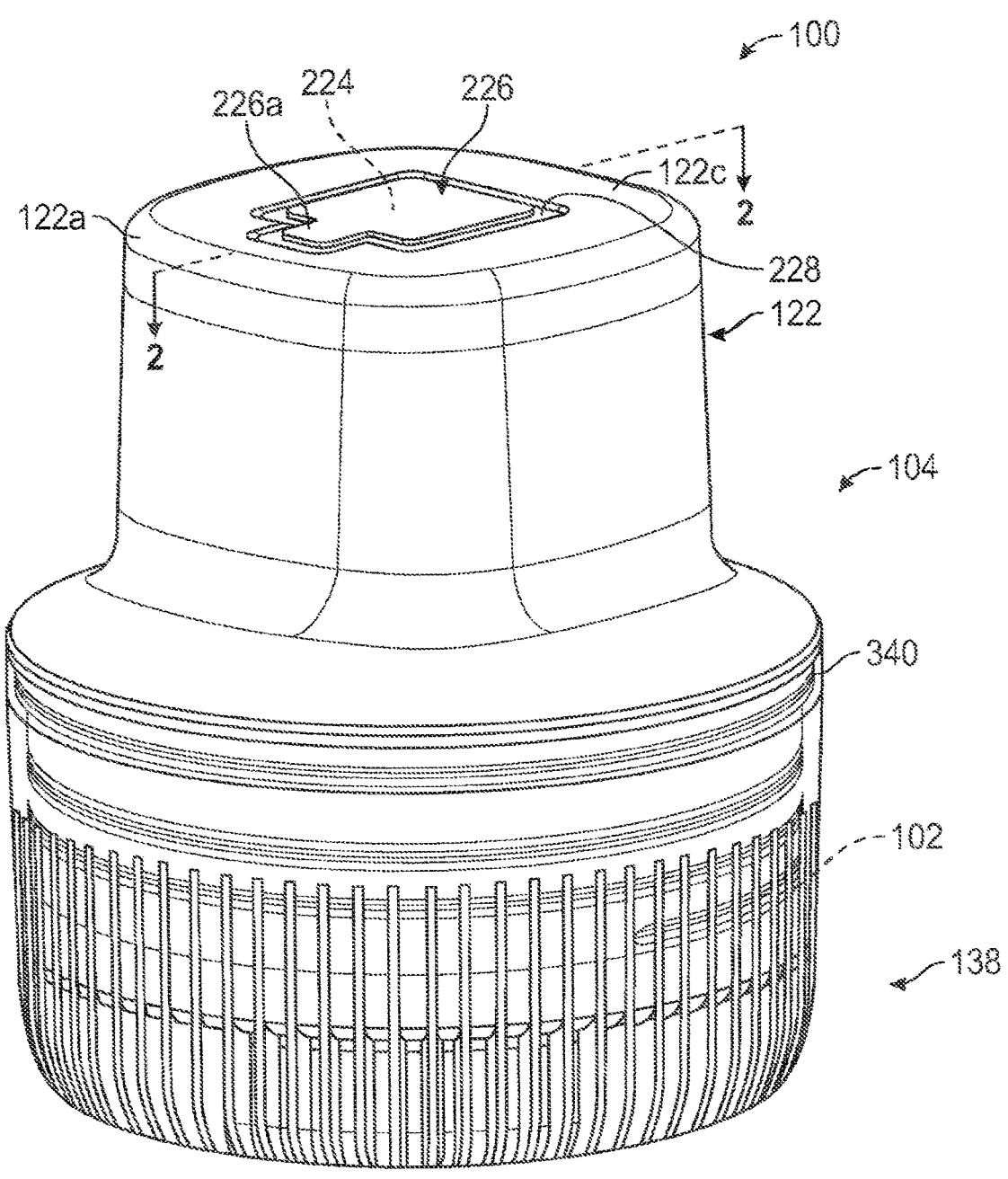
FIG. 1 is a perspective view of a disposable medical device introduction system that includes a disposable inserter for coupling a medic al device, in this example, a physiological characteristic sensor, to an anatomy of a user in accordance with various embodiments.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

As used herein, the term "axial" refers to a direction that is generally parallel to or coincident with an axis of rotation, axis of symmetry, or centerline of a component or components. For example, in a cylinder or disc with a centerline and generally circular ends or opposing faces, the "axial" direction may refer to the direction that generally extends in parallel to the centerline between the opposite ends or faces. In certain instances, the term "axial" may be utilized with respect to components that are not cylindrical (or otherwise radially symmetric). For example, the "axial" direction for a rectangular housing containing a rotating shaft may be viewed as a direction that is generally parallel to or coincident with the rotational axis of the shaft. Furthermore, the term "radially" as used herein may refer to a direction or a relationship of components with respect to a line extending outward from a shared centerline, axis, or similar reference, for example in a plane of a cylinder or disc that is perpendicular to the centerline or axis. In certain instances, components may be viewed as "radially" aligned even though one or both of the components may not be cylindrical (or otherwise radially symmetric). Furthermore, the terms "axial" and "radial" (and any derivatives) may encompass directional relationships that are other than precisely aligned with (e.g., oblique to) the true axial and radial dimensions, provided the relationship is predominantly in the respective nominal axial or radial direction. As used herein, the term "transverse" denotes an axis that crosses another axis at an angle such that the axis and the other axis are neither substantially perpendicular nor substantially parallel.

The following description relates to various embodiments of a disposable medical device introduction system, which includes a physiological characteristic sensor or an infusion unit, and a disposable inserter. The systems described herein enable the disposable inserter to be recycled or disposed of in the user's own home (or current location) without requiring a disposal in a biohazard and/or sharps container once the physiological characteristic sensor or infusion unit is coupled to the user. It should be noted that while the physiological characteristic sensor is described herein as being a continuous glucose monitor, it will be understood that the physiological characteristic sensor may comprise a variety of other sensors, such as cardiac monitors, body temperature sensors, EKG monitors etc., medical devices, and/or other components that are intended to be affixed to the body of a user. In addition, the fluid infusion device for use with the infusion unit of the infusion set may be used for infusing fluid into the body of a user. In certain embodiments, the infused medication fluid is insulin. In alternative embodiments, however, many other fluids may be administered through infusion such as, but not limited to, disease treatments, drugs to treat pulmonary hypertension, iron chelation drugs, pain medications, anti-cancer treatments, medications, vitamins, hormones, or the like. For the sake of brevity, conventional features and characteristics related to infusion system operation, insulin pump and/or infusion set operation, fluid reservoirs, and fluid syringes may not be described in detail here. Examples of infusion pumps and/or related pump drive systems used to administer insulin and other medications may be of the type described in, but not limited to: U.S. Patent Publication Nos. 2009/0299290 and 2008/0269687; U.S. Pat. Nos. 4,562,751; 4,678,408; 4,685,903; 5,080,653; 5,505,709; 5,097,122; 6,485,465; 6,554,798; 6,558,351; 6,659,980; 6,752,787; 6,817,990; 6,932,584; 7,621,893; 7,828,764; and 7,905,868; which are each incorporated by reference herein. Thus, while the non-limiting examples described below relate to a medical device used to treat diabetes (more specifically, a continuous glucose monitor or infusion unit associated with an infusion set), embodiments of the disclosed subject matter are not so limited.

Generally, the glucose sensor employed with the adhesive patch is a continuous glucose sensor of the type used by diabetic users. For the sake of brevity, conventional aspects and technology related to glucose sensors and glucose sensor fabrication may not be described in detail here. In this regard, examples of glucose sensors and their manufacturing may be of the type described in, but not limited to: U.S. Pat. Nos. 6,892,085, 7,468,033 and 9,295,786; and United States patent application number 2009/0299301 (which are each incorporated by reference herein). In addition, for the sake of brevity, conventional aspects and technology related to sensor inserters may not be described in detail here. In this regard, examples of sensor inserters may be of the type described in, but not limited to: U.S. Pat. No. 10,413,183 and U.S. application Ser. No. 16/892,854 filed on Jun. 4, 2020 (which are each incorporated by reference herein).

With reference to FIG. 1, FIG. 1 is a perspective view of a disposable medical device introduction system 100. In the example of FIG. 1, the disposable medical device introduction system 100 includes a physiological characteristic sensor assembly 102 and a disposable inserter 104. Generally, with reference to FIG. 2, the components of the physiological characteristic sensor assembly 102 are coupled together as a single unit. The physiological characteristic sensor assembly 102 and the disposable inserter 104 may be packaged together for use by a consumer or user. The disposable inserter 104 is in a first position in FIG. 2.

The physiological characteristic sensor assembly 102 may comprise any suitable physiological characteristic sensor, such as a continuous glucose monitor, for use with the disposable inserter 104, and thus, the physiological characteristic sensor assembly 102 will not be discussed in great detail herein. Briefly, the physiological characteristic sensor assembly 102 includes a physiological characteristic sensor 106 and an adhesive skin patch or adhesive patch 108. The physiological characteristic sensor 106 includes a sensor electronics module (not shown), such as a wireless transmitter that communicates with a fluid infusion device (such as an infusion pump), a monitor device, or the like, which connects to the physiological characteristic sensor 106 after the insertion or deployment of a portion of the physiological characteristic sensor 106 in the body of the user. In certain embodiments, the physiological characteristic sensor 106 includes a glucose sensor 110 and a sensor housing 112. It should be noted that the physiological characteristic sensor 106 is not limited to a glucose sensor, but rather, various other physiological characteristic sensors may be employed. The glucose sensor 110 may be provided as an integral part of the sensor housing 112. The sensor housing 112 gives structural support to the glucose sensor 110, and facilitates entry of the glucose sensor 110 into the body of the user. The glucose sensor 110 is an electrochemical sensor that includes the glucose oxidase enzyme, as is well understood by those familiar with glucose sensor technology. The glucose oxidase enzyme enables the glucose sensor 110 to monitor blood glucose levels in a diabetic patient or user by effecting a reaction of glucose and oxygen. Again, although certain embodiments pertain to glucose sensors, the technology described here can be adapted for use with any one of the wide variety of sensors known in the art. Generally, the glucose sensor 110 is positionable in subcutaneous tissue of the user by an insertion needle 162 of the disposable inserter 104 to measure the glucose oxidase enzyme.

The sensor housing 112 is coupled to the disposable inserter 104 and is coupled to the adhesive patch 108. The sensor housing 112 may also feature electrical and physical interfaces and elements that accommodate the sensor electronics module, such as the wireless transmitter that communicates with the infusion pump, the monitor device, or the like. In certain embodiments, the sensor housing 112 is composed at least in part from a plastic material. For the embodiment described here, the bulk of the sensor housing 112 is formed as a molded plastic component. The sensor housing 112 may be formed from acrylonitrile butadiene styrene, nylon, an acrylonitrile butadiene styrene polycarbonate blend, polyvinyl chloride, polytetrafluoroethylene (PTFE), polypropylene, polyether ether ketone (PEEK), polycarbonate or the like.

The adhesive patch 108 is coupled to the sensor housing 112 and affixes the sensor housing 112, and thus, the glucose sensor 110, to an anatomy, such as the skin of the user. The adhesive patch 108 is contained within the disposable inserter 104 during packaging and shipping. The adhesive patch 108 may be composed of a flexible and breathable material with one or more adhesive layers, such as cloth, a bandage-like material, and the like. For example, suitable materials could include polyurethane, polyethylene, polyester, polypropylene, polytetrafluoroethylene (PTFE), or other polymers, to which one or more adhesive layers are applied.

With reference back to FIG. 2, in various embodiments, the physiological characteristic sensor assembly 102 is coupled to the disposable inserter 104 for shipping and delivering the physiological characteristic sensor assembly 102 to the user. The disposable inserter 104 is manipulatable by a user to couple the glucose sensor 110 and the physiological characteristic sensor 106 to the user. With additional reference to FIG. 3, the disposable inserter 104 includes a needle cartridge 120, a plunger 122, a first biasing member or insertion spring 124, a frame 126, a retractor 128, a second biasing member or retraction spring 130, a retainer 132, a carrier 134, a magnet 136 and a cap 138. In this example, the cap 138 includes a membrane 140, as will be discussed further herein.

Figure 2:
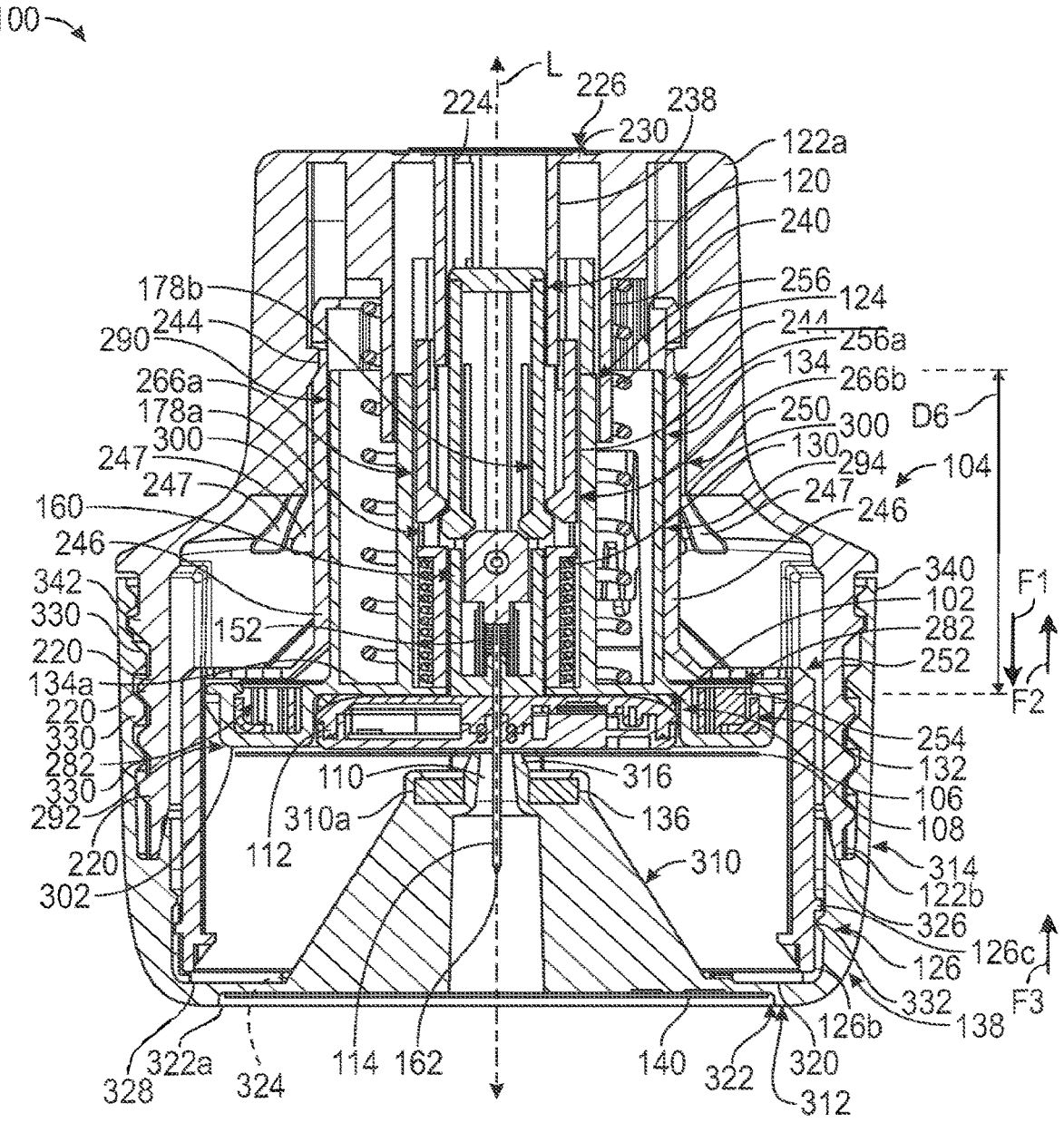
FIG. 2 is a cross-section view of the disposable medical device introduction system of FIG. 1, taken along line 2-2 of FIG. 1, which illustrates the disposable inserter in a first position and an insertion needle associated with a needle cartridge of the disposable inserter in a first, extended state.
Figures 4, 5:
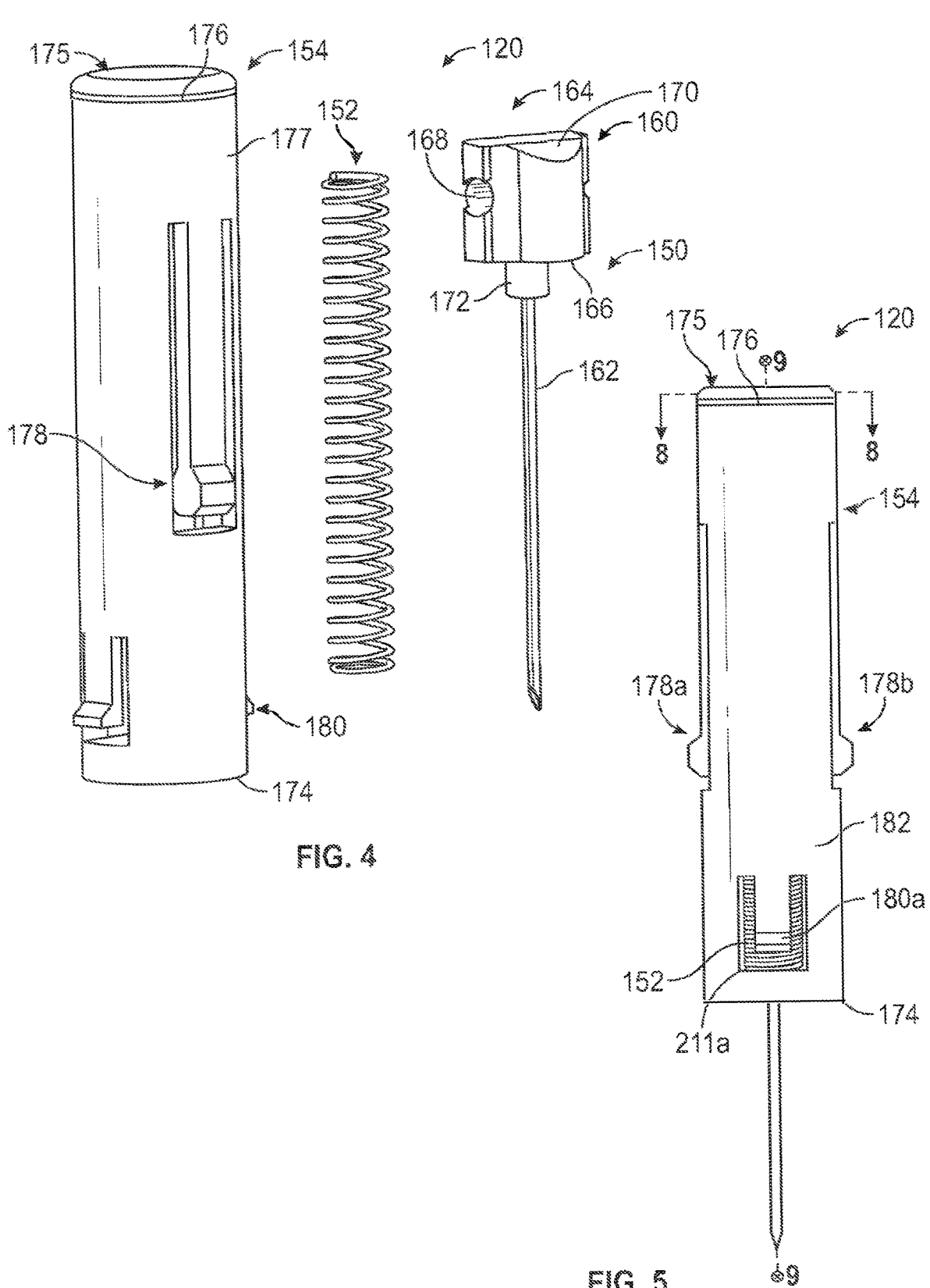
FIG. 4 is a partially exploded view of the needle cartridge of FIG. 2.
FIG. 5 is a front view of the needle cartridge of FIG. 2.

The needle cartridge 120 is movable relative to the plunger 122 to insert the glucose sensor 110 into the anatomy. With reference to FIG. 4, the needle cartridge 120 includes a needle inserter 150, a third biasing member or third spring 152 and a cartridge housing 154. The needle inserter 150 includes a needle carrier 160 and an insertion needle 162. The needle carrier 160 is overmolded onto the insertion needle 162. The needle carrier 160 is substantially cylindrical. The needle carrier 160 includes a first carrier end 164 opposite a second carrier end 166 and defines a cross-bore 168. The first carrier end 164 includes at least one contact surface, and in this example, includes opposed contact surfaces defined as chamfered surfaces 170. The chamfered surfaces 170 define a first contact surface for the cartridge housing 154, as will be discussed. Generally, the chamfered surfaces 170 are defined on opposed sides of the needle carrier 160, however, the chamfered surfaces 170 may comprise a single surface defined about a perimeter of the first carrier end 164, if desired. The second carrier end 166 is coupled to the insertion needle 162. The second carrier end 166 may include a collar 172 that extends outward from the second carrier end 166 and surrounds a portion of the insertion needle 162. The collar 172 is a spring guide for the third spring 152. The cross-bore 168 is defined through the needle carrier 160 from a first side to a second side to as to extend along an axis that is transverse or oblique to an axis defined by the insertion needle 162. The cross-bore 168 provides for ease of manufacturing by enabling the needle carrier 160 to be molded onto the insertion needle 162. The insertion needle 162 is generally a stainless steel needle, which extends for a distance beyond a distal end of the glucose sensor 110 to couple the glucose sensor 110 to the anatomy (FIG. 2).

The third spring 152 may be a helical coil spring, which is composed of a suitable biocompatible material, such as a spring steel that is wound to form the third spring 152. The third spring 152 is received between the needle carrier 160 and a second cartridge end 174 of the cartridge housing 154 (FIG. 5). The third spring 152 is held in compression by the needle carrier 160 to maintain the insertion needle 162 in a first extended state (shown in FIG. 5), and once released by the needle carrier 160, expands to move the needle carrier 160 relative to the cartridge housing 154 and within the cartridge housing 154, thereby moving the insertion needle 162 to a second retracted state (shown in FIG. 6) for disposal, as will be discussed further herein.

With reference to FIG. 4, the cartridge housing 154 is substantially cylindrical, and extends along a cartridge longitudinal axis CL. The cartridge longitudinal axis CL is parallel to a longitudinal axis L of the disposable inserter 104 (FIG. 2). The cartridge housing 154 is composed of a suitable polymer based material, including, but not limited to acrylonitrile butadiene styrene, nylon, an acrylonitrile butadiene styrene polycarbonate blend, polyvinyl chloride, polytetrafluoroethylene (PTFE), polypropylene, polyether ether ketone (PEEK), polycarbonate or the like. The cartridge housing 154 includes a cap 175, a first cartridge end 176 opposite the second cartridge end 174, a cartridge body 177 that interconnects the first cartridge end 176 with the second cartridge end 174, at least one lock arm 178 and at least one coupling tab 180. The cartridge housing 154 also defines a cartridge bore 182 that extends through the cartridge body 177 from the first cartridge end 176 to the second cartridge end 174.

Figures 6, 7:
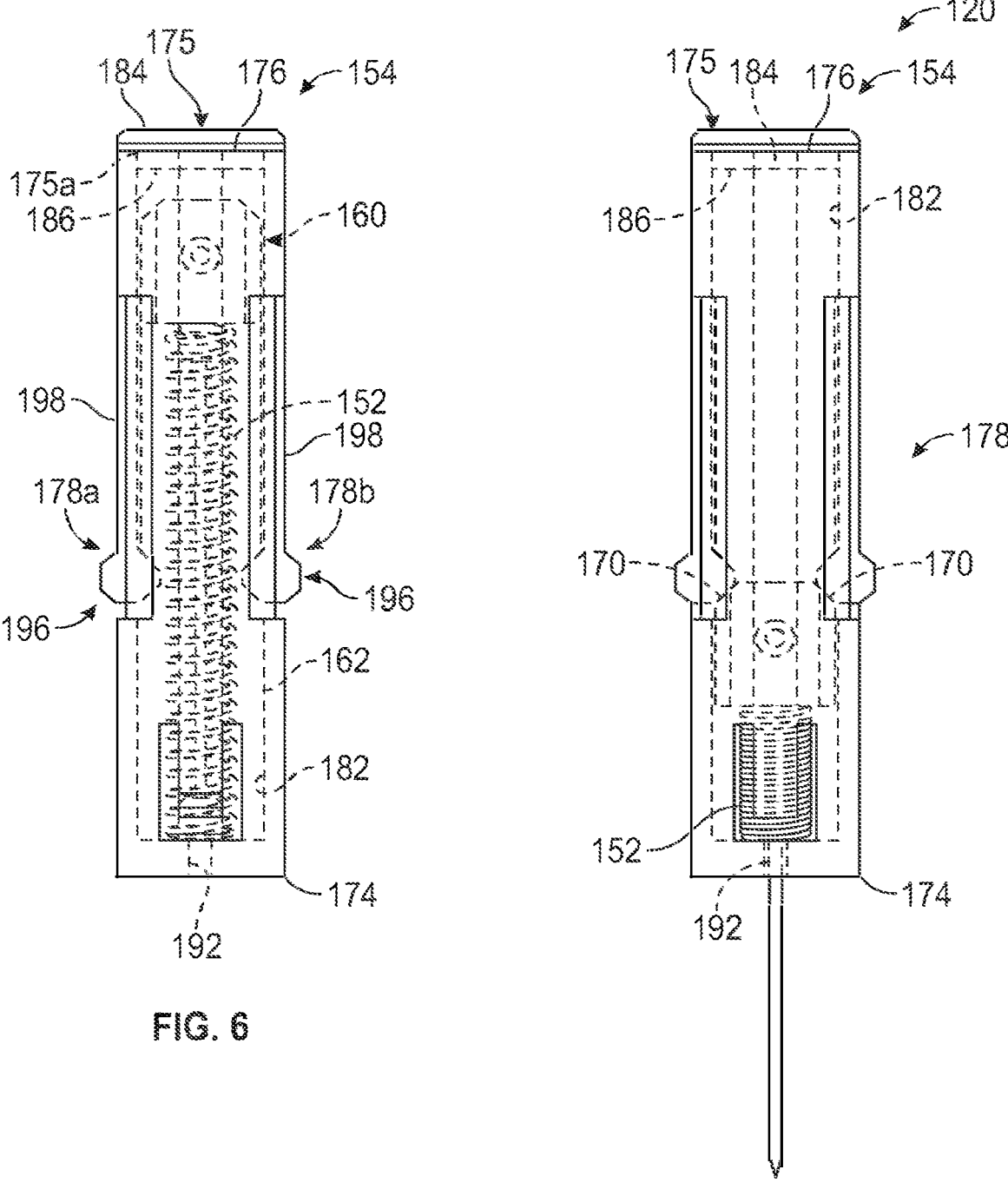
FIG. 6 is a front view of the needle cartridge of FIG. 2, which illustrates in phantom an insertion needle associated with the needle cartridge in a second, retracted state.
FIG. 7 is a front view of the needle cartridge of FIG. 2, which illustrates in phantom the insertion needle associated with the needle cartridge in the first, extended state.

The cap 175 is coupled to the cartridge body 177 at the first cartridge end 176 to enclose the cartridge bore 182 (FIG. 6). The cap 175 is generally discretely formed from the cartridge body 177, and is coupled to the first cartridge end 176 via ultrasonic welding, adhesives, etc. The cap 175 provides a stop for a travel of the needle carrier 160 within the cartridge bore 182 (FIG. 6). In this regard, the cap 175 includes a first exterior surface 184 opposite a second interior surface 186. The first exterior surface 184 is substantially planar or flat. The second interior surface 186 is defined along a cap projection 175a that extends into the cartridge bore 182 to enclose the cartridge bore 182 (FIG. 9). The second interior surface 186 provides a stop surface for further advancement of the needle carrier 160 within the cartridge bore 182. The second cartridge end 174 includes a third interior surface 188 opposite a fourth exterior surface 190, and defines a bore 192 that extends through the third interior surface 188 and the fourth exterior surface 190. The third interior surface 188 provides a seat for the third spring 152, and includes a guide collar 189. The guide collar 189 serves to guide a movement of the third spring 152. The fourth exterior surface 190 is substantially planar or flat. The bore 192 is defined through the third interior surface 188 and the fourth exterior surface 190 to enable the insertion needle 162 to pass through the bore 192 into the cartridge bore 182 when the insertion needle 162 is in the second, retracted state (shown in FIG. 6).

The cartridge body 177 is substantially cylindrical, and interconnects the first cartridge end 176 with the second cartridge end 174. The at least one lock arm 178 and the at least one coupling tab 180 are integrally formed with the cartridge housing 154. In certain embodiments, each of the at least one lock arm 178 and the at least one coupling tab 180 are integrally formed with the cartridge body 177. With reference to FIG. 8, the at least one lock arm 178 includes two lock arms 178a, 178b. The lock arms 178a, 178b extend from the first cartridge end 176 toward the second cartridge end 174. The lock arms 178a, 178b are opposed from each other about a perimeter or circumference of the cartridge body 177. Each of the lock arms 178a, 178b include a first lock arm end 194 and a second lock arm end 196 interconnected by an arm 198. Each of the lock arms 178a, 178b are cantilevered relative to the cartridge body 177, and thus, recesses 179a, 179b may be defined about the second lock arm end 196 and the arm 198 to enable the second lock arm end 196 to move relative to the cartridge body 177. As will be discussed, a movement of the lock arms 178a, 178b relative to the cartridge body 177 results in a movement of the insertion needle 162 from the first, extended state (FIG. 5) to the second, retracted state (FIG. 6).

The first lock arm end 194 is integrally formed with the cartridge body 177, and extends along an axis parallel to the cartridge longitudinal axis CL. The second lock arm end 196 has a bulbous portion 200, which defines a first contact surface 202 and a second contact surface 204. The first contact surface 202 is defined so as to extend a distance beyond an exterior surface 177a of the cartridge body 177 when the insertion needle 162 is in the first extended state (FIG. 8) to contact a portion of the retractor 128. In certain embodiments, the first contact surface 202 is a flat angled surface, which is defined along an exterior surface 196a of the second lock arm end 196. It should be noted that the first contact surface 202 may have other configurations, if desired. Generally, the first contact surface 202 is angled to correspond with an angle of the portion of the retractor 128 to provide surface to surface contact.

The second contact surface 204 is defined diagonally opposite from the first contact surface 202. The second contact surface 204 is defined so as to be positioned within the cartridge bore 182 to contact the chamfered surfaces 170 of the needle carrier 160 when the insertion needle 162 is in the first extended state. In certain embodiments, the second contact surface 204 is a flat angled surface, which is defined along an interior surface 196b of the second lock arm end 196. It should be noted that the second contact surface 204 may have other configurations, if desired. Generally, the first contact surface 202 and the second contact surface 204 each extend along an axis, and the axes of the first contact surface 202 and the second contact surface 204 are parallel to each other and transverse or oblique to the cartridge longitudinal axis CL. The second contact surface 204 is angled to correspond with the angle of the chamfered surfaces 170 to provide surface to surface contact between the respective one of the lock arms 178a, 178b and the respective one of the chamfered surfaces 170. The arm 198 interconnects the first lock arm end 194 and the second lock arm end 196. The arm 198 is surrounded by the respective recess 179a, 179b such that the arm 198 is a cantilevered beam.

With reference to FIG. 9, the at least one coupling tab 180 includes two coupling tabs 180a, 180b. The coupling tabs 180a, 180b are defined proximate the second cartridge end 174. The coupling tabs 180a, 180b are opposed from each other about a perimeter or circumference of the cartridge body 177. Each of the coupling tabs 180a, 180b include a first tab end 206 and a second tab end 208 interconnected by a coupling arm 210. Each of the coupling tabs 180a, 180b are cantilevered relative to the cartridge body 177, and thus, recesses 211a, 211b may be defined about the second tab end 208 and the coupling arm 210 to enable the second tab end 208 to move relative to the cartridge body 177. Generally, the recesses 211a, 211b are defined such that the second tab end 208 is spaced apart from the third interior surface 188 of the second cartridge end 174. As will be discussed, a movement of the coupling tabs 180a, 180b relative to the cartridge body 177 enables a removal of the needle cartridge 120 from the plunger 122.

The first tab end 206 is integrally formed with the cartridge body 177, and extends along an axis parallel to the cartridge longitudinal axis CL. The second tab end 208 has an angled projection 212, which engages with a portion of the retractor 128. The projection 212 is substantially triangular in shape, and is defined so as to extend a distance beyond the exterior surface 177a of the cartridge body 177 when the insertion needle 162 is in the first, extended state (FIG. 8) to contact a portion of the retractor 128. The coupling arm 210 interconnects the first tab end 206 and the second tab end 208. The coupling arm 210 is surrounded by the respective recess 211a, 211b such that the coupling arm 210 is a cantilevered beam.

With reference back to FIG. 3, the plunger 122 is composed of a biocompatible polymer, and may be molded, cast, printed, etc. The plunger 122 surrounds the frame 126, and includes a plurality of threads 220 defined about a surface of the plunger 122 adjacent to a second, bottom end 122b. The threads 220 removably couple the cap 138 to the plunger 122, as will be discussed. The plunger 122 is shaped to correspond to the shape of the physiological characteristic sensor 106 (FIG. 2) so that the user intuitively knows the position and orientation of the physiological characteristic sensor 106 when the disposable inserter 104 is used to couple the physiological characteristic sensor 106 to the anatomy. This enables the user to position the disposable inserter 104 at a location by feel, without having to see the insertion site, such as a back of an arm, for example. In certain embodiments, a first, top end 122a of the plunger 122 defines an access opening 224 and a removable cover or access cover 226, which enables a removal of the needle cartridge 120 from the disposable inserter 104.

Figure 10:
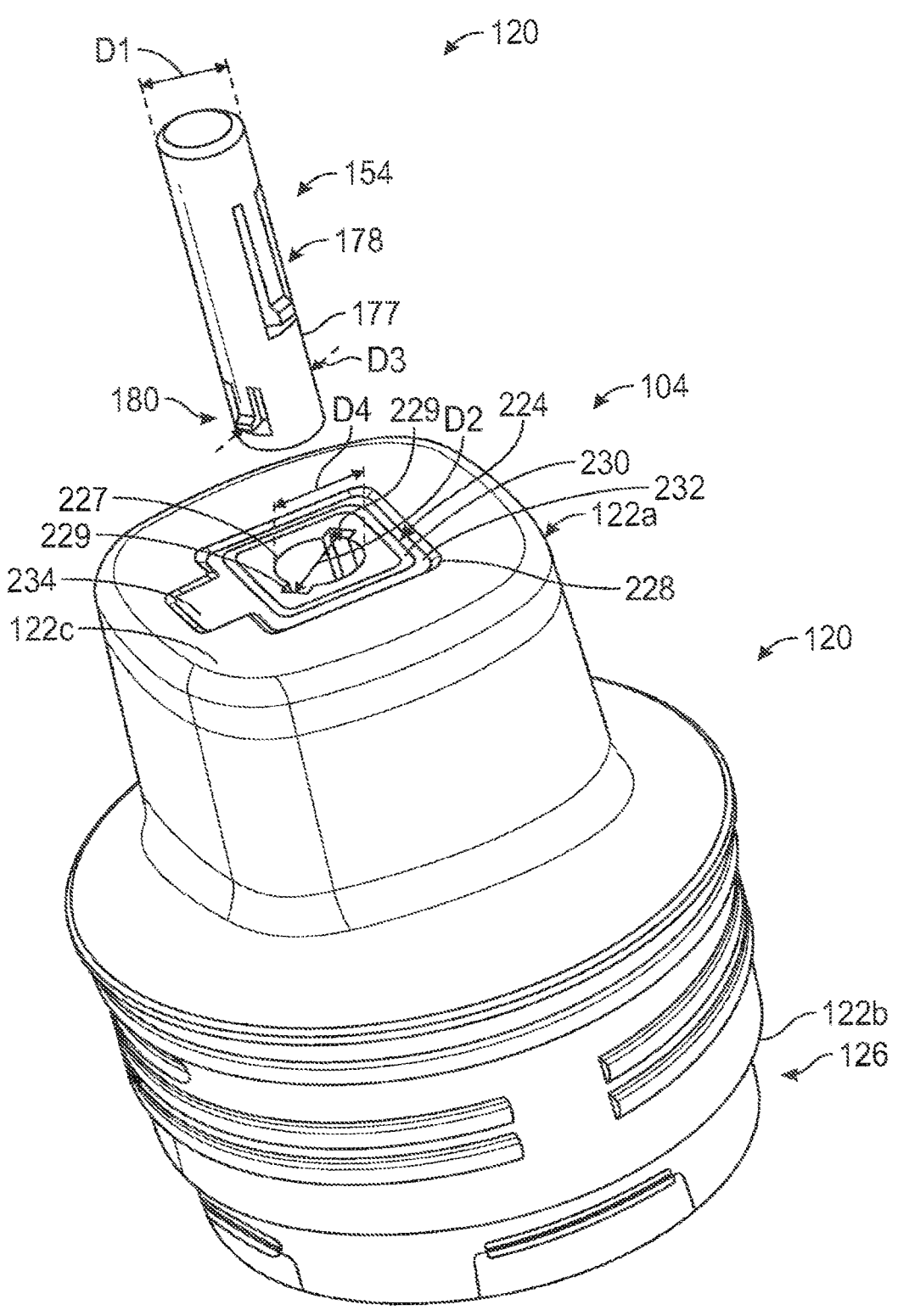
FIG. 10 is a perspective view of the disposable inserter in a third position, in which the needle cartridge is removed from the disposable inserter.

With reference to FIG. 10, the access opening 224 is shown in greater detail. In FIG. 10, the access cover 226 is removed from the plunger 122 and the needle cartridge 120 is shown removed from the disposable inserter 104 after a deployment of the physiological characteristic sensor 106 onto the anatomy. As shown, in this example, the access opening 224 includes a central circular portion 227 and a pair of opposed rectangular slots 229. The central circular portion 227 has a diameter D2 that is different than, and in this example, larger than, a diameter D1 of the cartridge body 177. The difference in the diameters D1, D2 enables the cartridge body 177 to pass through the access opening 224. The opposed rectangular slots 229 are in communication with the central circular portion 227 to enable the coupling tabs 180a, 180b to pass through the access opening 224. Generally, the coupling tabs 180a, 180b extend beyond a perimeter or circumference of the cartridge body 177 for a distance D3, which is different and less than a distance D4 defined by the opposed rectangular slots 229. The distance D3 is also different, and greater than, the diameter D1 (FIG. 9). Thus, generally, the access opening 224 enables the removal of the needle cartridge 120 from the disposable inserter 104. It should be noted that the access opening 224 may be configured or shaped differently, if desired, based on a shape of the needle cartridge 120.

The access opening 224 may be recessed relative to a surface 122c of the plunger 122 at the first end 122a so as to be disposed below a plane defined by the surface 122c. In this example, a recess 228 is defined at the first end 122a to surround the access opening 224, and the access opening 224 is defined through the recess 228. An inner rib 230 is defined about the access opening 224 to form a channel 232 between a sidewall of the recess 228 and the inner rib 230. The inner rib 230 is defined so as to be rectangular in this example, but the inner rib 230 may have any desired shape. The inner rib 230 extends outwardly from the recess 228 and is substantially coplanar with the surface 122c. The channel 232 is generally defined so as to be rectangular and to substantially surround the access opening 224. The channel 232 receives an adhesive, for example, to couple the removable access cover 226 (FIG. 1) to the plunger 122. It should be noted that in this example, the recess 228 also defines a recessed notch 234 that is spaced apart from the inner rib 230. The recessed notch 234 is spaced apart from the inner rib 230 to ensure that a minimal amount or no adhesive flows into the recessed notch 234. This ensures that a portion of the removable access cover 226 is unadhered to the plunger 122, which enables a user to insert a finger into the recessed notch 234 to grasp the access cover 226 and peel the access cover 226 from the plunger 122.

With reference to FIG. 1, the access cover 226 is shown attached to the plunger 122. In this example, the access cover 226 is substantially rectangular and includes a pull-tab 226a, however, the access cover 226 may have any desired shape that corresponds with the needle cartridge 120 and the access opening 224. The access cover 226 may be composed of any suitable material, and in certain embodiments, the access cover 226 is composed of a gas permeable polymeric material, such as Tyvek® manufactured by DuPont™ of Midland, Mich., which is coupled to the plunger 122 along the surface 122c of the recess 228, via adhesives, ultrasonic welding, heat bond, etc., for example. The access opening 224 is covered by the access cover 226. The access opening 224 cooperates with the access cover 226 to enable the sterilization of the physiological characteristic sensor 106 and the needle cartridge 120 contained within the disposable inserter 104. Generally, a seal is formed by the access cover 226 about the access opening 224 and during a sterilization procedure, the sterilization gas may penetrate into and out of the disposable inserter 104, via the access opening 224, and sterilize the physiological characteristic sensor 106 and an interior of the disposable inserter 104.

Figure 3:
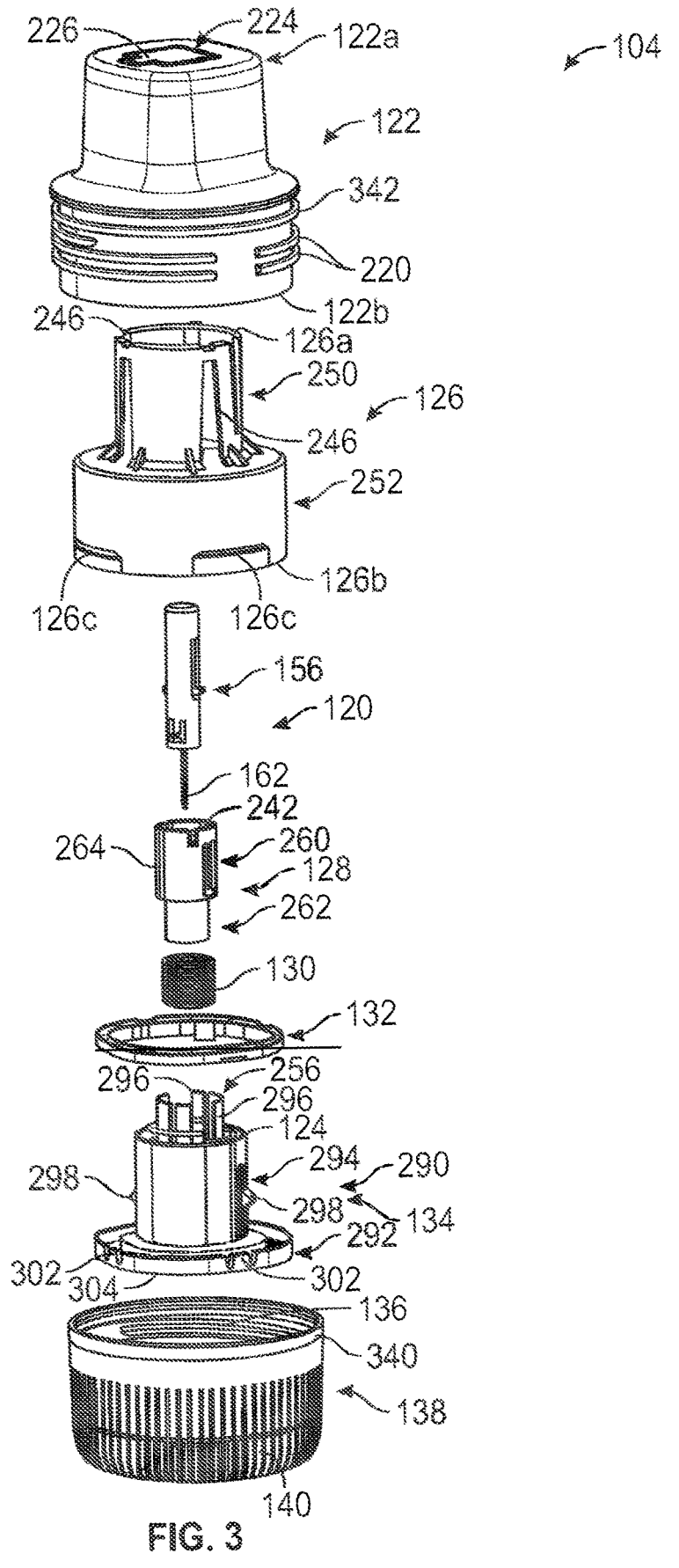
FIG. 3 is a partially exploded view of the disposable inserter of FIG. 2.

With reference back to FIG. 2, the plunger 122 also defines a first inner guide surface 238 and a second inner guide surface 240. Each of the first inner guide surface 238 and the second inner guide surface 240 extend inward from an inner surface of the plunger 122. In this example, each of the first inner guide surface 238 and the second inner guide surface 240 extend from the first end 122a toward the second end 122b. In certain embodiments, the first inner guide surface 238 includes a slot that cooperates with a rail 242 defined within the retractor 128 (FIG. 3). The engagement of the rail 242 with the slot guides the retractor 128 toward the first end 122a of the plunger 122 to facilitate the removal of the needle cartridge 120 after deployment of the physiological characteristic sensor 106. The second inner guide surface 240 cooperates with the carrier 134 to guide the carrier 134 during deployment of the physiological characteristic sensor 106. The plunger 122 also includes a plurality of projections 244 that extend radially inward spaced apart about an interior periphery of the plunger 122. The projections 244 cooperate with slots 246 defined in the frame 126. Generally, the projections 244 and the slots 246 cooperate to a guide a movement of the plunger 122 relative to the frame 126. The plunger 122 also includes frame projections 247. The frame projections 247 extend radially inward and are defined about a perimeter of the plunger 122. As will be discussed, the frame projections 247 cooperate with the frame 126 to release the physiological characteristic sensor 106 when the disposable inserter 104 is in a second position.

The insertion spring 124 is a helical coil spring, which is composed of a suitable biocompatible material, such as a spring steel that is wound to form the insertion spring 124. The insertion spring 124 is received between the second inner guide surface 240 of the plunger 122 and a surface 134a of the carrier 134. Generally, the insertion spring 124 expands as the carrier 134 moves toward a second, bottom end 126b of the frame 126 to couple the physiological characteristic sensor 106 to the user and exerts a spring force F1 along the longitudinal axis L to move the carrier 134 toward the bottom end 134b of the frame 126 for deployment of the physiological characteristic sensor 106.

Figure 14:
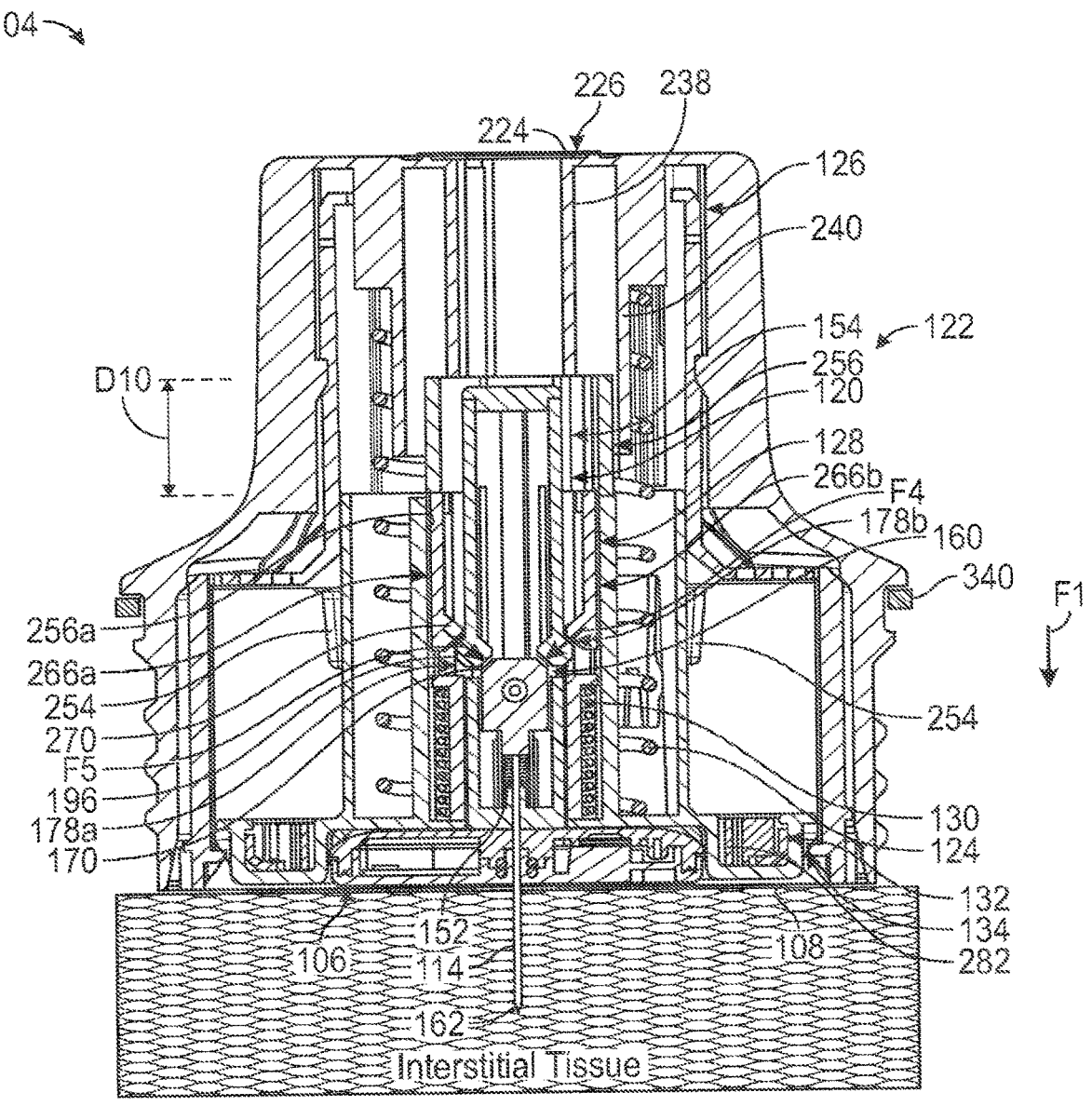
FIG. 14 is a cross-section view of the disposable medical device introduction system of FIG. 1, taken from the perspective of line 2-2 of FIG. 1, which illustrates the disposable inserter in a second position and the insertion needle associated with the needle cartridge of the disposable inserter in the first, extended state.

The frame 126 is received within the plunger 122. Generally, the frame 126 extends a distance beyond the plunger 122. The frame 126 is composed of a biocompatible polymer, and may be molded, cast, printed, etc. With reference to FIG. 3, the frame 126 includes a first frame portion 250 and a second frame portion 252. The slots 246 are defined in the first frame portion 250 and extend from a top surface 126a of the frame 126 to the second frame portion 252. The second frame portion 252 surrounds the carrier 134 such that the physiological characteristic sensor 106 (FIG. 2) is positioned within the second frame portion 252 of the frame 126. With reference to FIG. 14, the second frame portion 252 includes at least one or a plurality of ribs 254. The ribs 254 are spaced apart about the inner perimeter of the frame 126, and extend for a distance to engage with the retainer 132 as shown. In a first position, as shown in FIG. 2, the ribs 254 engage with the retainer 132 to retain the physiological characteristic sensor 106. In a second position, the ribs 254 are released, via contact between the frame projections 247 of the plunger 122 and the ribs 254, which causes the retainer 132 to release the physiological characteristic sensor 106 for deployment onto the anatomy.

Figure 11:
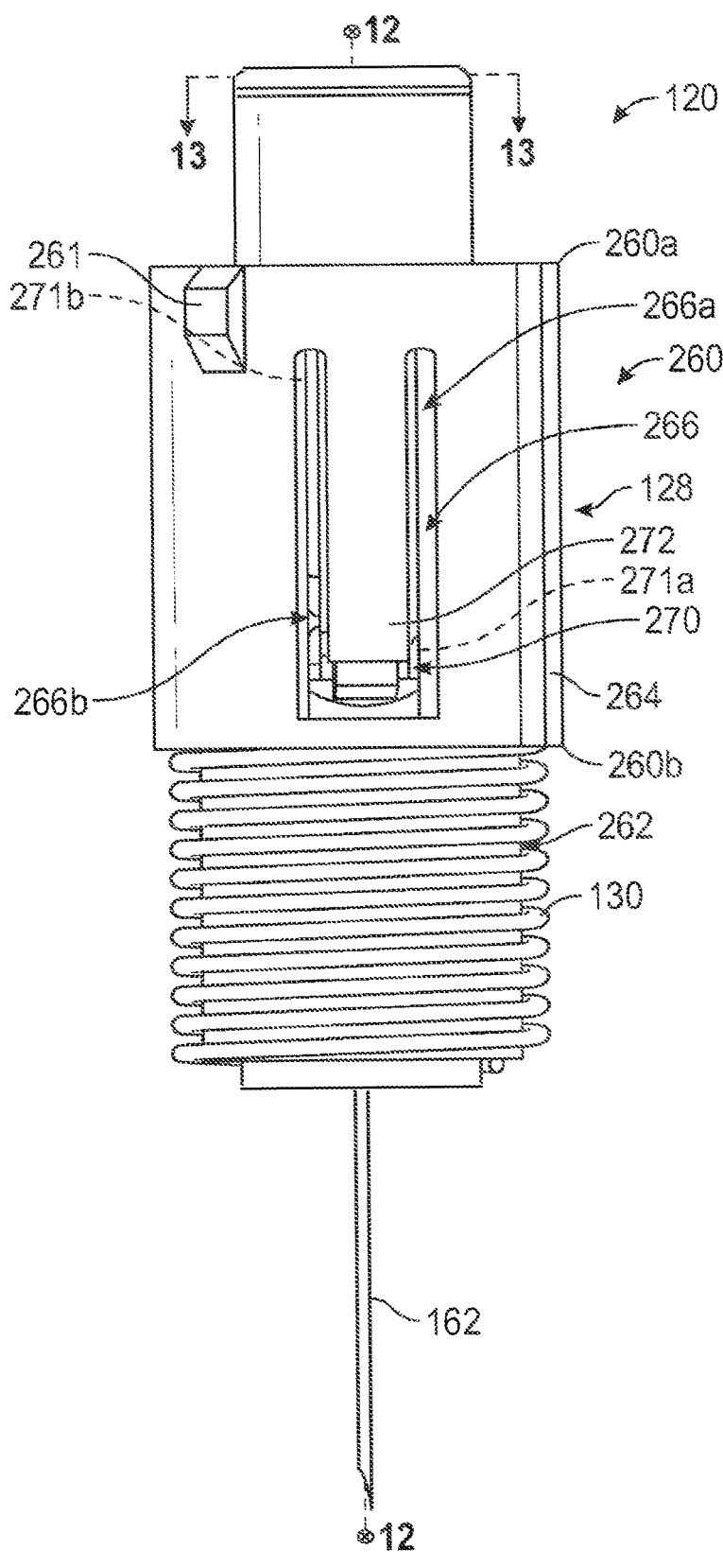
FIG. 11 is a front view of a retractor and a retraction spring coupled to the needle cartridge of FIG. 2.
Figures 12, 13:
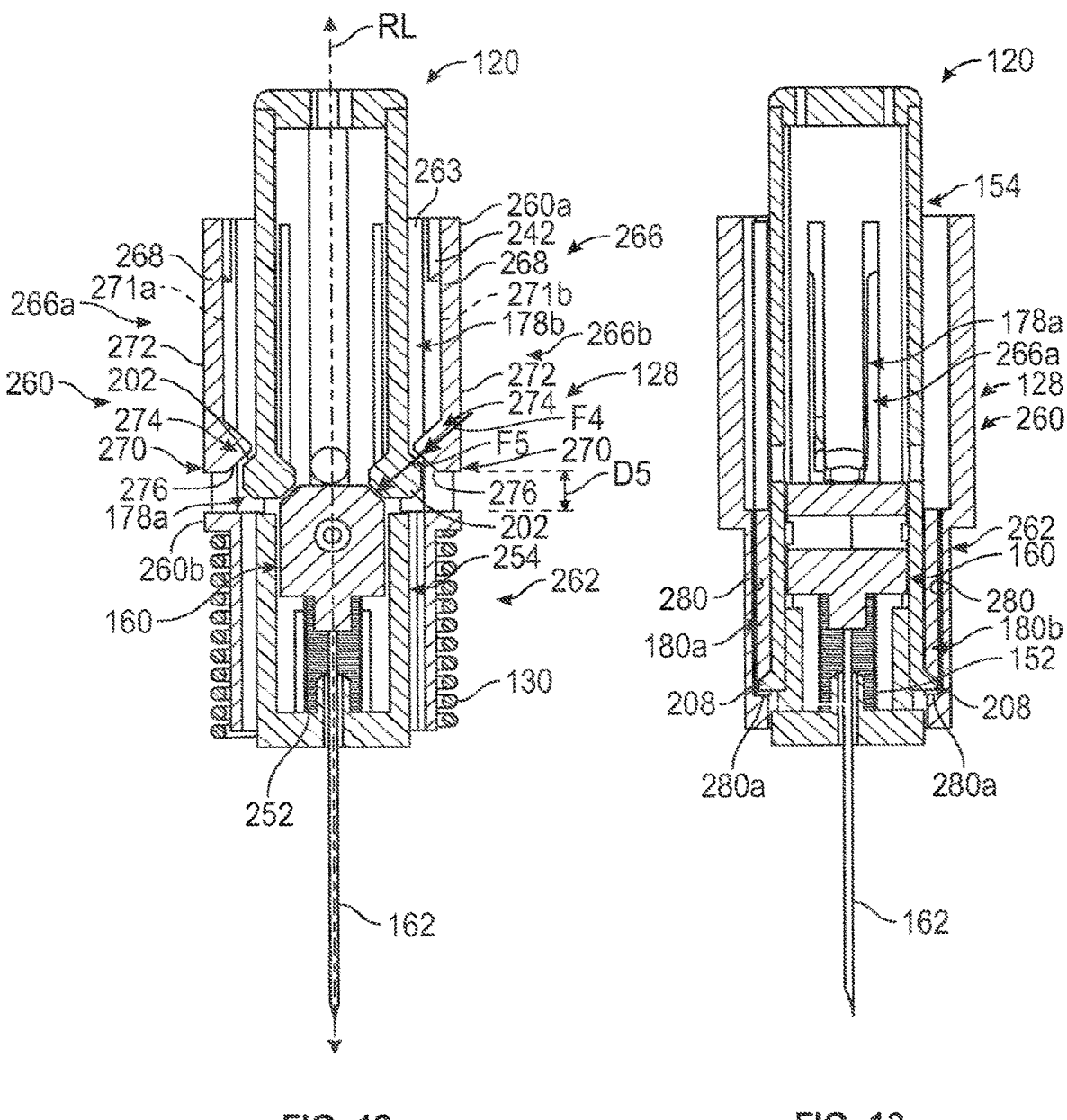
FIG. 12 is a cross-sectional view of the retractor, the retraction spring and the needle cartridge of FIG. 11, taken along line 12-12 of FIG. 11.
FIG. 13 is a cross-sectional view of the retractor, the retraction spring and the needle cartridge of FIG. 11, taken along line 13-13 of FIG. 11.

The retractor 128 is coupled to a second annular projection 256 of the carrier 134. The retractor 128 is composed of a biocompatible polymer, and may be molded, cast, printed, etc. With reference to FIG. 11, the retractor 128 includes a first portion 260, a second portion 262 and defines a bore 263 that extends through the first portion 260 and the second portion 262. The needle cartridge 120 is received within the bore 263. The first portion 260 has a greater diameter than the second portion 262. The first portion 260 includes one or more guide projections 264, which are spaced apart about a perimeter of the first portion 260. The guide projections 264 contact a second annular projection 256 of the carrier 134. The first portion 260 may also include a locating projection 261, which assists with assembly of the retractor 128 to the carrier 134. The first portion 260 also includes at least one retaining arm 266. With reference to FIG. 12, the retractor 128 is shown coupled to the needle cartridge 120 and the retraction spring 130. In this example, the at least one retaining arm 266 includes two retaining arms 266a, 266b. The retaining arms 266a, 266b extend from a first end 260a toward a second end 260b of the first portion 260. Generally, the retaining arms 266a, 266b are defined so as to be spaced apart from the second portion 262 by a distance D5 so that the retaining arms 266a, 266b engage with the lock arms 178a, 178b. The retaining arms 266a, 266b are opposed from each other about a perimeter or circumference of the first portion 260. Each of the retaining arms 266a, 266b include a first retaining arm end 268 and a second retaining arm end 270 interconnected by an arm 272. Each of the retaining arms 266a, 266b are cantilevered relative to the first portion 260, and thus, recesses 271a, 271b (FIG. 11) may be defined about the second retaining arm end 270 and the arm 272 to enable the second retaining arm end 270 to move relative to the first portion 260 of the retractor 128. As will be discussed, a movement of the retaining arms 266a, 266b relative to the first portion 260 of the retractor 128 results in a movement of the insertion needle 162 from the first, extended state (FIG. 5) to the second, retracted state (FIG. 6).

The first retaining arm end 268 is integrally formed with the first portion 260, and extends along an axis parallel to a retractor longitudinal axis RL. The second retaining arm end 270 has a triangular portion 274, which defines a retaining contact surface 276. The triangular portion 274 extends inward into the bore 263 to contact the first contact surface 202 of the respective lock arm 178a, 178b when the insertion needle 162 is in the first extended state (FIG. 8). In certain embodiments, the retaining contact surface 276 is a flat angled surface, which is defined along one side of the triangular portion 274. Generally, the retaining contact surface 276 is angled to correspond with the angle of the first contact surface 202 of the lock arms 178a, 178b to provide surface to surface contact. It should be noted that the retaining contact surface 276 may have other configurations, if desired. Generally, the retaining contact surface 276 extends along an axis, which is transverse or oblique to the retainer longitudinal axis RL. The arm 272 interconnects the first retaining arm end 268 and the second retaining arm end 270. The arm 272 is surrounded by the respective recess 271a, 271b such that the arm 272 is a cantilevered beam.

The second portion 262 is coupled to the cartridge housing 154 of the needle cartridge 120. The diameter of the second portion 262 is sized such that the retraction spring 130 is positioned between the first portion 260 and the carrier 134 so as to surround the second portion 262, as shown in FIG. 2. With reference to FIG. 13, the second portion 262 defines at least one internal slot or opposed internal slots 280. The internal slots 280 slidably receive the second tab end 208 of the respective coupling tabs 180a, 180b. The internal slots 280 include a stop surface 280a, which limits an advancement of the needle cartridge 120 within the retractor 128. Generally, the internal slots 280 guide the needle cartridge 120 during the deployment of the physiological characteristic sensor 106 (FIG. 2) into the anatomy. Once the physiological characteristic sensor 106 (FIG. 2) is deployed, the internal slots 280 enable the needle cartridge 120 to be removed or uncoupled from the retractor 128 as the internal slots 280 end at the first portion 260. As the first portion 260 has a greater diameter than the second portion 262, the second tab end 208 of the coupling tabs 180a, 180b pass freely through the first portion 260 to enable the removal of the needle cartridge 120.

With reference to FIG. 2, the retraction spring 130 may be a helical coil spring, which is composed of a suitable biocompatible material, such as a spring steel that is wound to form the retraction spring 130. The retraction spring 130 is received between the second portion 262 of the retractor 128 and a surface 134a of the carrier 134. After deployment, the retraction spring 130 expands and exerts a spring force F2 along the longitudinal axis L to move the retractor 128 toward the first inner guide surface 238 of the plunger 122 to enable the removal of the needle cartridge 120.

With reference to FIG. 2, the retainer 132 is coupled to and received about a perimeter of the carrier 134. The retainer 132 assists in coupling or retaining the physiological characteristic sensor 106 on the carrier 134. The retainer 132 may be composed of a biocompatible polymer, and may be molded, cast, printed, etc. The retainer 132 is the same as the sensor retainer described in U.S. application Ser. No. 16/892,854 filed on Jun. 4, 2020, previously incorporated herein by reference, and thus, the retainer 132 will be discussed briefly herein. Generally, the retainer 132 includes at least one or plurality of retainer arms 282, which are spaced apart about a perimeter of the retainer 132. Each of the retainer arms 282 is cantilevered from the retainer 132, and includes a contact surface that retains the physiological characteristic sensor 106 in a second state. In a first state, the contact surface of the retainer arms 282 does not contact the physiological characteristic sensor 106 such that the physiological characteristic sensor 106 is released or uncoupled from the retainer 132 when the retainer arms 282 are in the first state. In the first state, a gap is defined between a terminal end of each of the retainer arms 282 and a surface of the retainer 132. In the second state, each of the ribs 254 of the frame 126 contact a respective one of the retainer arms 282 to bias or compress the retainer arms 282. In the second state, the gap is substantially eliminated and the terminal end of each of the retainer arms 282 contacts a surface of the retainer 132. In the second state, the contact surface is held against the physiological characteristic sensor 106 to retain the physiological characteristic sensor 106 on the retainer 132. Generally, the frame projections 247 of the plunger 122 contact the ribs 254 of the frame 126, which pushes the ribs 254 outward, thereby releasing the retainer arms 282. The release of the retainer arms 282 moves the retainer arms 282 from the second state to the first state, which releases the contact surface from the physiological characteristic sensor 106.

The carrier 134 moves relative to the frame 126 to deploy the physiological characteristic sensor 106 onto the user. The carrier 134 may be composed of a biocompatible polymer, and may be molded, cast, printed, etc. The carrier 134 includes a support body 290 and a retaining flange 292. The support body 290 is annular, and includes at least one annular projection, and in this example, includes a first annular projection 294 and the second annular projection 256 that are concentric. The first annular projection 294 couples the carrier 134 to the frame 126, and the second annular projection 256 couples the retractor 128 to the carrier 134. The second annular projection 256 may also include opposed slots 296 (FIG. 3), which cooperate with the retractor 128 to couple the retractor 128 to the carrier 134. In this example the second annular projection 256 extends for a distance D6 from the retaining flange 292. By extending the distance D6, the second annular projection 256 applies a force to the retaining arms 266a, 266b of the first portion 260 of the retractor 128. Stated another way, the distance D6 ensures that a sidewall 256a of the second annular projection 256 applies a force to the retaining arms 266a, 266b, which in turn, applies a force to the needle carrier 160 via the lock arms 178a, 178b to maintain the insertion needle 162 in the first, extended state.

With reference to FIG. 3, the carrier 134 also includes insertion snaps 298. The insertion snaps 298 extend outwardly from the first annular projection 294, and are received within the slots 246 of the frame 126. Generally, the insertion snaps 298 are spaced apart from a surface of the slots 246 to inhibit a relative movement between the carrier 134 and the frame 126. The cap 138 applies a force F3 to the physiological characteristic sensor 106 in the first position, which causes the insertion snaps 298 of the carrier 134 to be spaced apart from the surface of the frame 126 and free floating. This ensures that if the disposable inserter 104 is accidentally mishandled in the first position, the carrier 134 is not inadvertently released.

With reference to FIG. 2, a ramp surface 300 defined interiorly within the plunger 122 contacts the insertion snaps 298 (FIG. 3) as the plunger 122 moves relative to the frame 126. The contact between the ramp surface 300 and the insertion snaps 298 causes the insertion snaps 298 (FIG. 3) to deflect, thereby releasing the insertion snaps 298 (FIG. 3) from the slots 246 and from the frame 126. The release of the carrier 134 from the frame 126 enables the insertion spring 124 to apply the force F1 to couple the physiological characteristic sensor 106 to the anatomy.

With reference to FIG. 3, the retaining flange 292 is substantially rectangular in shape, and is coupled to the retainer 132. The retaining flange 292 includes a plurality of retaining tabs 302 and defines a contact surface 304 (FIG. 2). The retaining tabs 302 couple the retainer 132 to the carrier 134. With reference to FIG. 2, the contact surface 304 is continuous and is defined about a perimeter of the retaining flange 292. The contact surface 304 presses the adhesive patch 108 against the anatomy of the user upon deployment of the physiological characteristic sensor 106 to ensure that the adhesive patch 108 is coupled to the user over an entirety of the adhesive patch 108.

In this example, the magnet 136 is coupled to the cap 138. The magnet 136 comprises any suitable permanent magnet composed of a ferromagnetic material that is axially magnetized. As the magnet 136 and the cap 138 are the same as the magnet 214 and the cap 216 discussed in U.S. application Ser. No. 16/892,854 filed on Jun. 4, 2020, previously incorporated herein, the magnet 136 and the cap 138 will be discussed briefly herein. Generally, the magnet 136 is annular and cooperates with the physiological characteristic sensor 106 to activate the physiological characteristic sensor 106 based on a removal of the cap 138. For example, the physiological characteristic sensor 106 may include a magnetic field sensor that is responsive to the magnetic field generated by the magnet 136 to activate the physiological characteristic sensor 106 based on a change in the magnetic field. The cap 138 may be composed of a biocompatible polymer, and may be molded, cast, printed, etc. The cap 138 includes a projection 310, a cap base 312 and a sidewall 314. The projection 310 extends axially upward from the cap base 312 and defines an annular channel 310a that is coupled to the magnet 136. The projection 310 terminates in a tip 316. The tip 316 applies the force F3 against the physiological characteristic sensor 106, which causes the insertion snaps 298 (FIG. 3) to float within the slots 246.

The cap base 312 has a first base surface 320 opposite a second base surface 322 and defines a plurality of openings 324. The first base surface 320 is coupled to or integrally formed with the projection 310. The second base surface 322 defines a circular recess 322a, which receives the membrane 140. The membrane 140 is a gas permeable polymeric material, such as Tyvek® manufactured by DuPont™ of Midland, Mich., which is coupled to the cap 138 along a surface of the circular recess 322a, via adhesives, heat bond, etc., for example. The openings 324 are covered by the membrane 140. The openings 324 cooperate with the membrane 140 to enable the sterilization of the physiological characteristic sensor 106 contained within the disposable inserter 104. Generally, the plunger 122 and the cap 138 cooperate to form a seal, such that during a sterilization procedure, the sterilization gas may penetrate into and out of the disposable inserter 104, via the openings 324, and sterilize the physiological characteristic sensor 106 and an interior of the disposable inserter 104. The second end 122b of the plunger 122 is coupled to the cap 138 in an interference fit, which inhibits fluids, such as air and liquids, to flow into the disposable inserter 104. In this example, the sidewall 314 of the cap 138 includes a lip 326, which circumscribes the cap 138 and receives the second end 122b of the plunger 122 with the interference fit. The cap base 312 may also include a frame receiving channel 328, which receives the second end 126b of the frame 126.

The sidewall 314 includes the lip 326, a plurality of threads 330 and a frame projection 332. The plurality of threads 330 are defined so as to be spaced apart from the lip 326. The plurality of threads 330 engage with the threads 220 of the plunger 122 to removably couple the cap 138 to the plunger 122. The frame projection 332 cooperates with a thread 126c defined on the frame 126. The frame projection 332 acts as a thread such that the cap 138 is screwed onto both the frame 126 and the plunger 122. By screwing the cap 138 onto both the frame 126 and the plunger 122, the frame 126 is locked in position relative to the plunger 122, which inhibits the frame 126 from moving relative to plunger 122 in an instance where the disposable inserter 104 is mishandled or dropped.

In certain embodiments, the cap 138 also includes a tamper evident band or tamper band 340. The tamper band 340 may be composed of a biocompatible polymer, and may be molded, cast, additive manufactured, etc. The tamper band 340 may be coupled to the cap 138 via a plurality of bridges, which are breakable upon unscrewing or uncoupling the cap 138 from the plunger 122. In this example, the plunger 122 also defines a tamper bead retaining catch 342 about an outer perimeter of the plunger 122. The tamper bead retaining catch 342 extends outward such that as the user is removing the cap 138, the tamper band 340 contacts the tamper bead retaining catch 342. The contact between the tamper band 340 and the tamper bead retaining catch 342, along with the continued applied force by the user, separates the cap 138 from the tamper band 340 at the bridges, leaving the tamper band 340 about the plunger 122 to visually indicate the cap 138 has been removed.

In certain embodiments, with reference to FIG. 4, in order to assemble the disposable inserter 104, the needle carrier 160 is coupled to the insertion needle 162. With the cartridge housing 154 formed, the third spring 152 is inserted into the cartridge housing 154. The needle carrier 160 is inserted through the cartridge housing 154 such that the insertion needle 162 is in the first, extended state (FIG. 7). In certain embodiments, the lock arms 178a, 178b may be held during assembly by an external force to maintain the insertion needle 162 in the first, extended state. The cap 175 is coupled to the cartridge housing 154. With reference to FIG. 13, the needle cartridge 120 is inserted into the retractor 128. The retaining arms 266a, 266b may be held by an external force during assembly so that the retaining arms 266a, 266b to apply a force F4 against the respective lock arms 178a, 178b. The application of the force F4 by the retaining arms 266a, 266b causes the lock arms 178a, 178b apply a force F5 to the needle carrier 160, which maintains the insertion needle 162 in the first, extended state.

With reference to FIG. 3, with the retainer 132 coupled to the carrier 134, the carrier 134 is coupled to the frame 126. The retraction spring 130 is positioned within the second annular projection 256 of the carrier 134. The retractor 128, including the needle cartridge 120, is coupled to the second annular projection 256 of the carrier 134 so that the insertion needle 162 remains in the first, extended state. The insertion spring 124 is positioned within the first annular projection 294 of the carrier 134. With the access cover 226 coupled to the access opening 224, the plunger 122 is coupled to the frame 126. With reference to FIG. 2, the physiological characteristic sensor 106 is coupled to the carrier 134 so as to be retained by the retainer 132. The cap 138, with the membrane 140 and the tamper band 340 coupled to the cap 138, is threaded onto the plunger 122 and the frame 126. The cap 138 is coupled to the plunger 122 such that the projection 310 applies the force F3 to the physiological characteristic sensor 106. The disposable inserter 104 is in a first position in FIG. 2. The disposable inserter 104, including the physiological characteristic sensor 106, may be sterilized and shipped to an end user.

Once received, the user may remove the cap 138. As the user unscrews the cap 138, the tamper band 340 breaks along the bridges and remains coupled to the plunger 122. With the cap 138 removed, the physiological characteristic sensor 106 is exposed for insertion. In addition, the removal of the cap 138 removes the magnetic field generated by the magnet 136, which activates the physiological characteristic sensor 106 to monitor the glucose sensor 114. The user may position the disposable inserter 104 at the desired insertion site, which may or may not be visible to the user. The user may depress the plunger 122, which with reference to FIG. 14, releases the carrier 134 and the retainer arms 282 of the retainer 132 (FIG. 14). The release of the carrier 134 and the retainer arms 282 separates the physiological characteristic sensor 106 from the disposable inserter 104. Once the carrier 134 is released from the frame 126, the insertion spring 124 applies the force F1 to couple the physiological characteristic sensor 106 to the user. As the sidewall 256a of the second annular projection 256 of the carrier 134 remains adjacent to the retractor 128, the retaining arms 266a, 266b continue to apply the force F4 to the lock arms 178a, 178b of the cartridge housing 154. The lock arms 178a, 178b, in turn, continue to apply the force F5 to the needle carrier 160. Stated another way, as the sidewall 256a of the second annular projection 256 of the carrier 134 inhibits the outward deflection of the retaining arms 266a, 266b, the second retaining arm end 270 of the retaining arms 266a, 266b applies the force F4 to the second lock arm end 196 of the lock arms 178a, 178b, which in turn, applies the force F5 to the chamfered surfaces 170 of the needle carrier 160. The application of the forces F4, F5 by the retractor 128 and the cartridge housing 154 of the needle cartridge 120, respectively, maintain the insertion needle 162 in the first, extended state during the deployment of the physiological characteristic sensor 106 onto the anatomy. The disposable inserter 104 is in a second position in FIG. 14.

Figure 15:
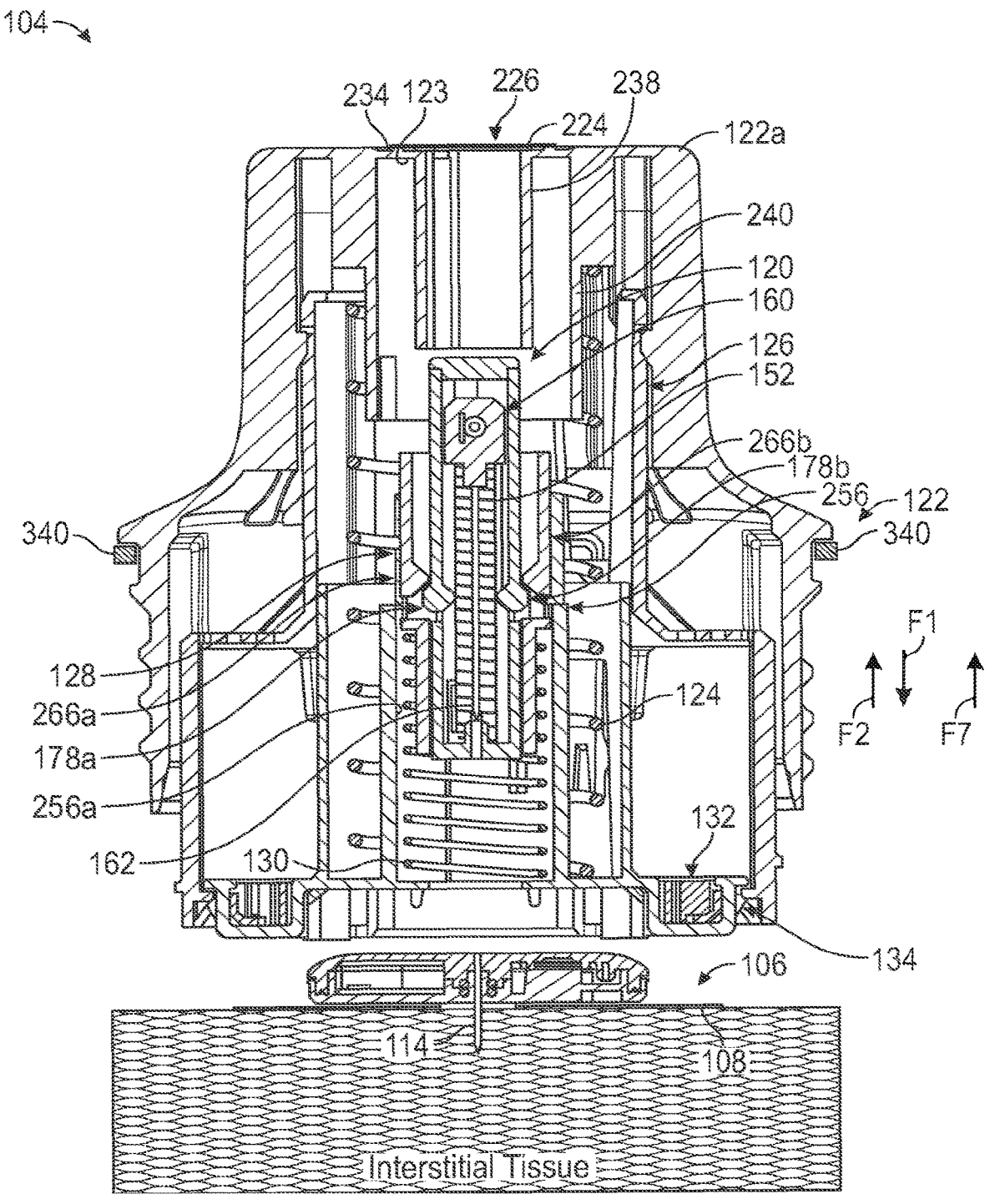
FIG. 15 is a cross-section view of the disposable medical device introduction system of FIG. 1, taken from the perspective of line 2-2 of FIG. 1, which illustrates the disposable inserter between the second position and a third position, the insertion needle associated with the needle cartridge of the disposable inserter in the second, retracted state and the physiological characteristic sensor is deployed on the user.

Generally, once the insertion spring 124 deploys the carrier 134 and the physiological characteristic sensor 106 is coupled to the anatomy, the retraction spring 130 applies the force F2 and retracts the retractor 128 upward toward the access opening 224. The movement of the retractor 128 toward the access opening 224 directs or urges the needle cartridge 120 toward the access opening 224. Once the retraction spring 130 has moved the retractor 128 past the sidewall 256a of the carrier 134, a force F7 of the third spring 152 is greater than a force applied by the retaining arms 266a, 266b and the lock arms 178a, 178b, as the retaining arms 266a, 266b and the lock arms 178a, 178b are able to expand outwardly or deflect unrestrained by the carrier 134. The force F7 applied as the third spring 152 expands moves the needle carrier 160, along with the insertion needle 162, toward the cap 175 of the cartridge housing 154, thereby moving the insertion needle 162 to the second, retracted state as shown in FIG. 15. Stated another way, once the retractor 128 has moved past the sidewall 256a, the retaining arms 266a, 266b are released, which in turn releases the lock arms 178a, 178b, which in turn, releases the needle carrier 160 such that the force F7 of the third spring 152 may move the insertion needle 162 to the second, retracted state. In the second, retracted state, the insertion needle 162 is wholly contained within the cartridge housing 154. In the second, retracted state, the second lock arm end 196 of the lock arms 178a, 178b along with the third spring 152 inhibit the needle carrier 160 from moving rearward or back into the first, extended state to thereby inhibit a potential inadvertent exposure of the insertion needle 162 from the cartridge housing 154.

Figure 16:
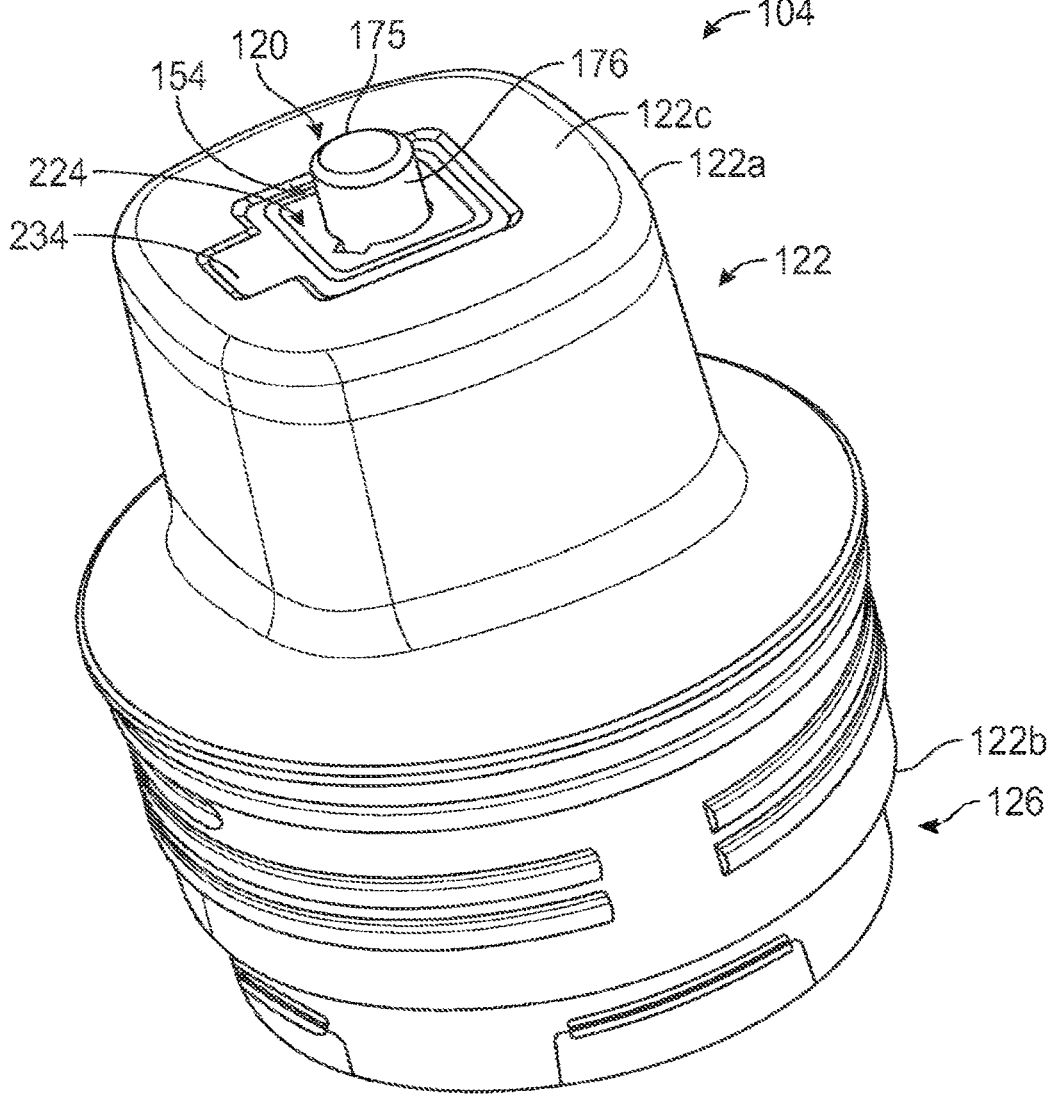
FIG. 16 is a perspective view of the disposable inserter of FIG. 15, in which the disposable inserter is between the second position and the third position, and the needle cartridge, with the insertion needle in the second, retracted state, is graspable for removal from the disposable inserter.
Figure 17:
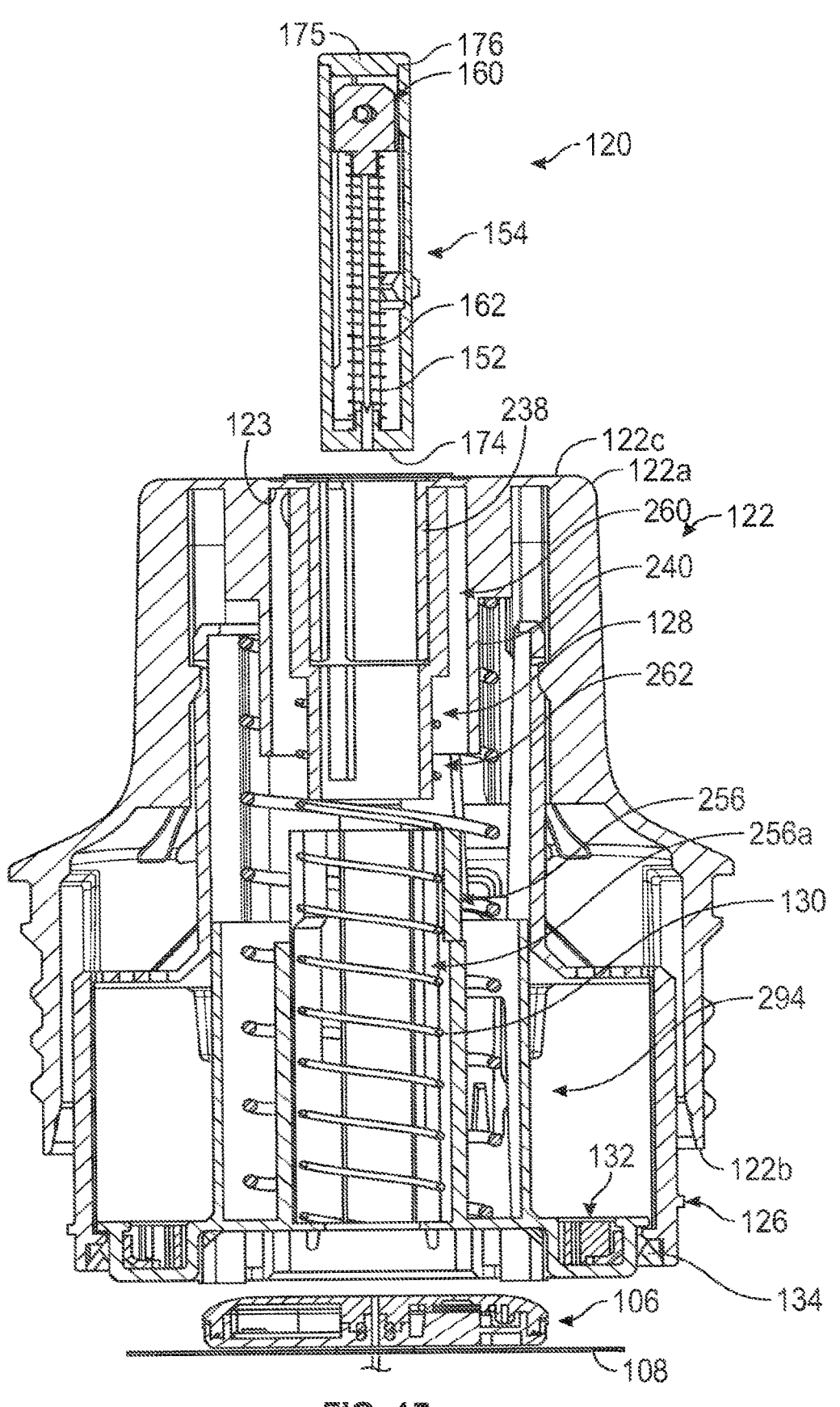
FIG. 17 is a cross-section view of the disposable medical device introduction system of FIG. 1, taken from the perspective of line 2-2 of FIG. 1, which illustrates the disposable inserter in the third position, the needle cartridge, with the insertion needle in the second, retracted state, removed from the disposable inserter and the physiological characteristic sensor is deployed on the user.

The continued application of the force F2 of the retraction spring 130 moves the retractor 128, and thus, the needle cartridge 120 toward the first end 122a of the plunger 122. When the access cover 226 is attached to the plunger 122 as shown in FIG. 15, the needle cartridge 120 is biased by the retractor 128, via the retraction spring 130, toward the first end 122a. Generally, as the needle cartridge 120 extends a distance D10 (FIG. 14) beyond the retractor 128 when assembled, the retraction spring 130 is not able to fully expand to position the retractor 128 against a surface 123 of the plunger 122 at the first end 122a due to contact between the access cover 226 and the cap 175 of the cartridge 156. When the access cover 226 is removed, by placing a finger in the recessed notch 234 and pulling the access cover 226 (FIG. 15) away from the access opening 224, for example, the retraction spring 130 is able to fully expand, and the force F2 of the retraction spring 130 moves the retractor 128 toward the first end 122a of the plunger 122 to seat the retractor 128 against the surface 123 (as shown in FIG. 17). As shown in FIG. 16, with the retraction spring 130 fully expanded, the cap 175 and the first cartridge end 176 extend beyond the surface 122c of the plunger 122 at the first end 122a, which enables the user to easily grasp and remove the needle cartridge 120 from the disposable inserter 104 (FIG. 10).

With reference to FIG. 17, a cross-sectional view of the needle cartridge 120 removed from the disposable inserter 104 is shown. In FIG. 17, the disposable inserter 104 is in a third position. In the third position, the retraction spring 130 is fully extended such that the retractor 128 is coupled to the first inner guide surface 238 and is positioned at the surface 123 at the first end 122a. As the needle cartridge 120 is removed from the disposable inserter 104, the disposable inserter 104 may be disposed of at the user's home or other location via recycling for example. Thus, the disposable inserter 104 does not require the user to dispose of the disposable inserter 104 in a biohazard and/or sharps container as the needle cartridge 120, which contains the insertion needle 162, has been removed from the disposable inserter 104. This provides convenience to the user, and enables the user to install the physiological characteristic sensor 106 and dispose of the disposable inserter 104 conveniently in any recycling or garbage bin. The user may also easily dispose of the needle cartridge 120 upon removal of the needle cartridge 120 from the disposable inserter 104.

Figure 18:
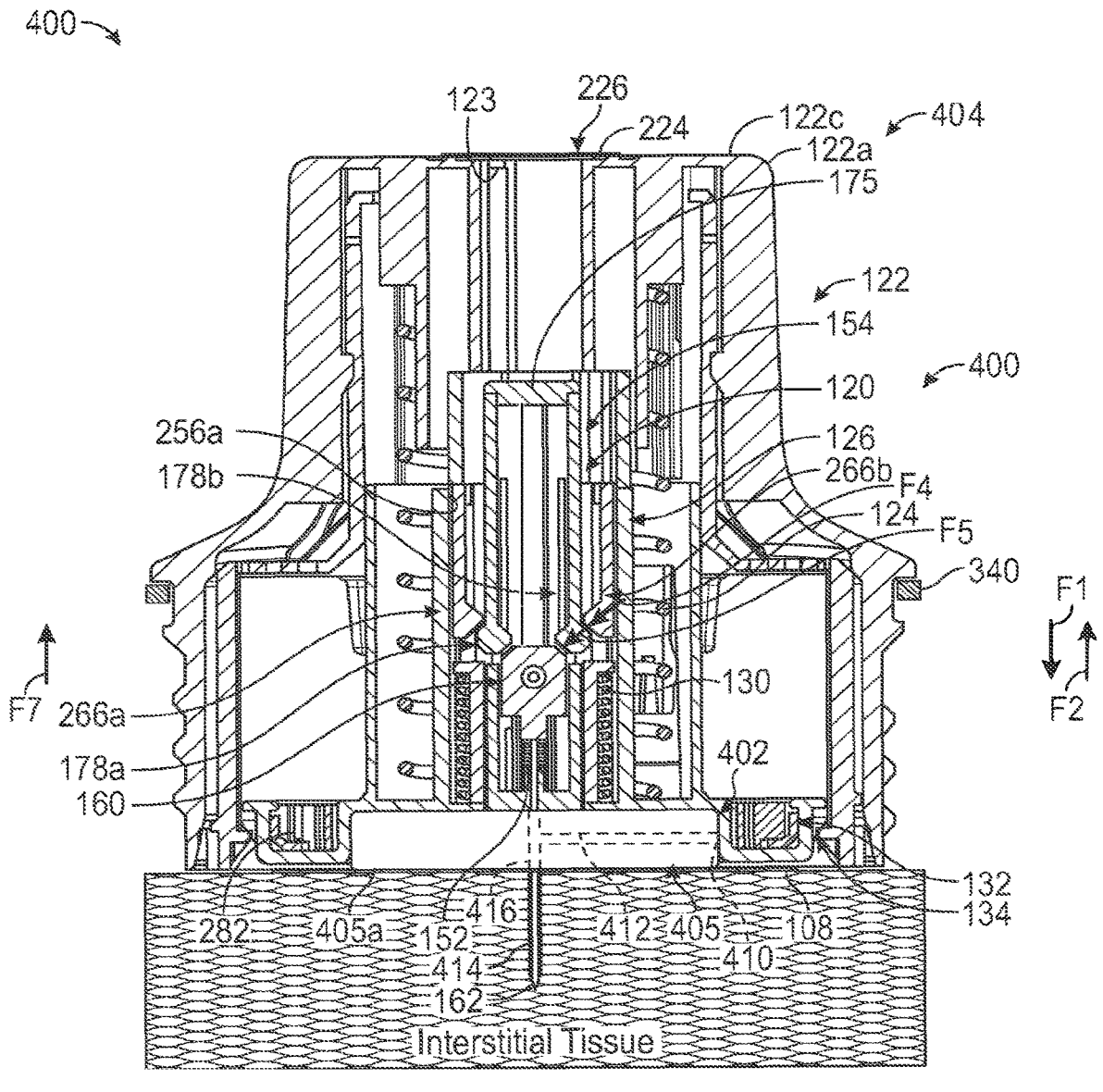
FIG. 18 is a cross-section view of another exemplary disposable medical device introduction system, taken from the perspective of line 2-2 of FIG. 1, which illustrates a disposable inserter in a second position and the insertion needle associated with the needle cartridge of the disposable inserter in the first, extended state for deploying a portion of an infusion unit assembly onto an anatomy.

It should be noted that while the disposable medical device introduction system 100 is described herein as being used to deploy the physiological characteristic sensor assembly 102, including the physiological characteristic sensor 106, on the anatomy, a disposable medical device introduction system may be configured differently. In this regard, with reference to FIG. 18, a disposable medical device introduction system 400 is shown. As the disposable medical device introduction system 400 includes the same or similar components as the disposable medical device introduction system 100 discussed with regard to FIGS. 1-17, the same reference numerals will be used. In this example, the disposable medical device introduction system 400 includes an infusion unit assembly 402 and a disposable inserter 404. In FIG. 18, the disposable inserter 404 is shown in the second position, in which the disposable inserter 404 is coupling a portion of the infusion unit assembly 402 to the anatomy.

Figure 19:
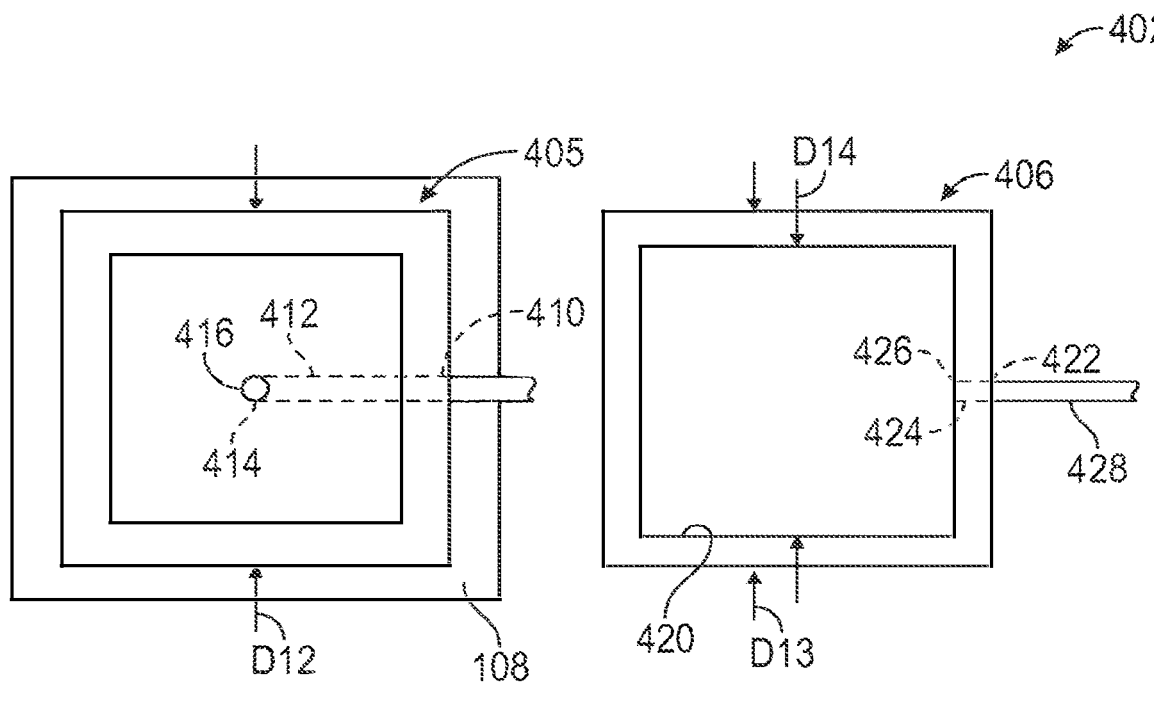
FIG. 19 is an exploded view of the infusion unit assembly for use with the disposable inserter of FIG. 18 in accordance with various embodiments.

The infusion unit assembly 402 may comprise any suitable infusion unit associated with an infusion set for dispensing a fluid to a user for use with the disposable inserter 404, and thus, the infusion unit assembly 402 will not be discussed in great detail herein. In this example, with reference to FIG. 19, the infusion unit assembly 402 includes an infusion hub 405, a tubing connector 406 and the adhesive patch 108. Generally, the infusion hub 405 and the disposable inserter 404 may be packaged together for use by a consumer or user. The infusion hub 405 and the tubing connector 406 cooperate to define a fluid flow path from a fluid reservoir of a fluid infusion device, such as an insulin pump, to a body of a user.

Briefly, the infusion hub 405 includes an inlet 410, a conduit 412 and a cannula 414 (FIG. 18). The infusion hub 405 may also define a bore 416, which enables the insertion needle 162 to pass through to insert the cannula 414 into the anatomy. The bore 416 may be covered by a septum. The inlet 410 fluidly couples the infusion hub 405 to the tubing connector 406 to define a fluid flow path between the infusion hub 405 and the tubing connector 406. Generally, the infusion hub 405 is composed of a biocompatible polymer, and may be cast, printed, molded, etc. The inlet 410, the conduit 412 and the bore 416 may each be integrally formed with the infusion hub 405, and the cannula 414 may comprise a portion of flexible tubing, which is formed discretely and coupled to the infusion hub 405 via ultrasonic welding, for example. The infusion hub 405 has a hub distance D12, which is different and less than a distance D13 of the tubing connector 406. The inlet 410 is defined through a perimeter of the infusion hub 405 and is in fluid communication with the conduit 412. The conduit 412 extends radially from the inlet 410 to the bore 416. The conduit 412 defines a fluid flow path from the inlet 410 to the bore 416. The bore 416 is defined axially though the infusion hub 405. The bore 416 enables the insertion needle 162 to pass through the infusion hub 405 to couple the cannula 414 to the anatomy, and also defines a fluid flow path between the conduit 412 and the cannula 414. The cannula 414 extends axially along a central axis defined by the bore 416 (FIG. 18). The cannula defines a fluid flow path from the infusion hub 405 to the anatomy (FIG. 18). The adhesive patch 108 is coupled to the infusion hub 405 along a bottom surface 405a (FIG. 18) of the infusion hub 405.

The tubing connector 406 defines an inner bore 420, an inlet 422, a tubing conduit 424 and an outlet 426. The inner bore 420 is sized to have a distance D14, which is different and greater than the distance D12 of the infusion hub 405, to enable the tubing connector 406 to be positioned about the infusion hub 405 to fluidly couple the infusion hub 405 to the tubing connector 406. The inlet 422 is defined through a perimeter of the tubing connector 406 and is in fluid communication with the tubing conduit 424. The inlet 422 is fluidly coupled to a tubing 428, which is a source of fluid for the infusion unit assembly 402. Generally, the tubing 428 is fluidly coupled to the fluid infusion device, such as an infusion pump, to receive a fluid, such as insulin. The tubing conduit 424 extends radially from the inlet 422 to the outlet 426. The tubing conduit 424 defines a fluid flow path from the inlet 422 to the outlet 426. When the tubing connector 406 is coupled to the infusion hub 405, the outlet 426 is fluidly coupled to the inlet 410 of the infusion hub 405. In certain embodiments, the tubing 428 may extend through an opening defined through the tubing connector 406 such that the tubing 428 is the tubing conduit 424, which terminates at the outlet 426.

With reference back to FIG. 18, in various embodiments, the infusion hub 405 is coupled to the disposable inserter 404 for shipping and delivering the infusion hub 405 to the user. The disposable inserter 404 is manipulatable by a user to couple the cannula 414 and the infusion hub 405 to the user. The disposable inserter 404 includes the needle cartridge 120, the plunger 122, the insertion spring 124, the frame 126, the retractor 128, the retraction spring 130, the retainer 132, the carrier 134 and the cap 138 (FIG. 2). The cap 138 includes the membrane 140 (FIG. 2). In this example, the disposable inserter 404 is the same as the disposable inserter 104, however, the cap 138 of disposable inserter 404 does not include the magnet 136. Thus, the disposable inserter 404 will not be discussed in great detail herein.

The infusion hub 405 is coupled to the carrier 134 and retained by the retainer 132. The disposable inserter 404, including the infusion hub 405, may be sterilized and shipped to an end user. Once received, the user may remove the cap 138 (FIG. 2). As the user unscrews the cap 138, the tamper band 340 breaks along the bridges and remains coupled to the plunger 122. With the cap 138 removed, the infusion hub 405 is exposed for insertion. The user may position the disposable inserter 404 at the desired insertion site, which may or may not be visible to the user. The user may depress the plunger 122, which releases the carrier 134 and the retainer arms 282 of the retainer 132. The release of the carrier 134 and the retainer arms 282 separates the infusion hub 405 from the disposable inserter 404. Once the carrier 134 is released from the frame 126, the insertion spring 124 applies the force F1 to couple the infusion hub 405 to the user. The insertion needle 162 is maintained in the first, extended state during the deployment of the infusion hub 405 onto the anatomy due to the forces F4, F5 applied to the needle carrier 160 by the lock arms 178a, 178b and the retaining arms 266a, 266b, respectively.

Generally, once the insertion spring 124 deploys the carrier 134 and the infusion hub 405 is coupled to the anatomy, the retraction spring 130 applies the force F2 and retracts the retractor 128 upward toward the access opening 224. Once the retraction spring 130 has moved the retractor 128 past the sidewall 256a of the carrier 134, the force F7 of the third spring 152 is greater than a force applied by the retaining arms 266a, 266b and the lock arms 178a, 178b, as the retaining arms 266a, 266b and the lock arms 178a, 178b are able to expand outwardly or deflect unrestrained by the carrier 134. The force F7 applied as the third spring 152 expands moves the needle carrier 160, along with the insertion needle 162, toward the cap 175 of the cartridge housing 154, thereby moving the insertion needle 162 to the second, retracted state (FIG. 15). In the second, retracted state, the insertion needle 162 is fully contained within the cartridge housing 154.

Figure 20:
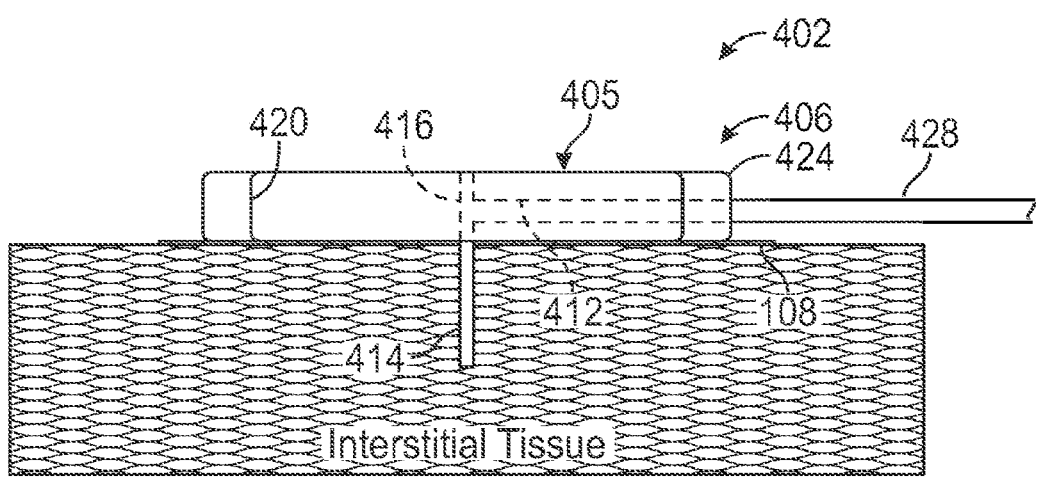
FIG. 20 is a schematic illustration of the infusion unit assembly deployed on the anatomy to define a fluid flow path to a user.

The continued application of the force F2 of the retraction spring 130 moves the retractor 128, and thus, the needle cartridge 120 toward the first end 122a of the plunger 122. The access cover 226 is removed, and the retraction spring 130 is able to fully expand, to move the retractor 128 toward the first end 122a of the plunger 122 to seat the retractor 128 against the surface 123 (as shown in FIG. 17). With the retraction spring 130 fully expanded, the cap 175 and the first cartridge end 176 extend beyond the surface 122c of the plunger 122 at the first end 122a, which enables the user to easily grasp and remove the needle cartridge 120 from the disposable inserter 404. With reference to FIG. 20, with the infusion hub 405 coupled to the anatomy by the disposable inserter 404, the tubing connector 406 may be coupled to the infusion hub 405 to define a fluid flow path through the tubing 428 to the anatomy of the user via the cannula 414. Generally, the fluid flow path through the tubing 428 is coupled to the cannula 414 of the infusion hub 405 via the conduit 412. The tubing 428 may be fluidly coupled to the fluid reservoir of the fluid infusion device, such as an insulin reservoir of an insulin pump.

Figure 21:
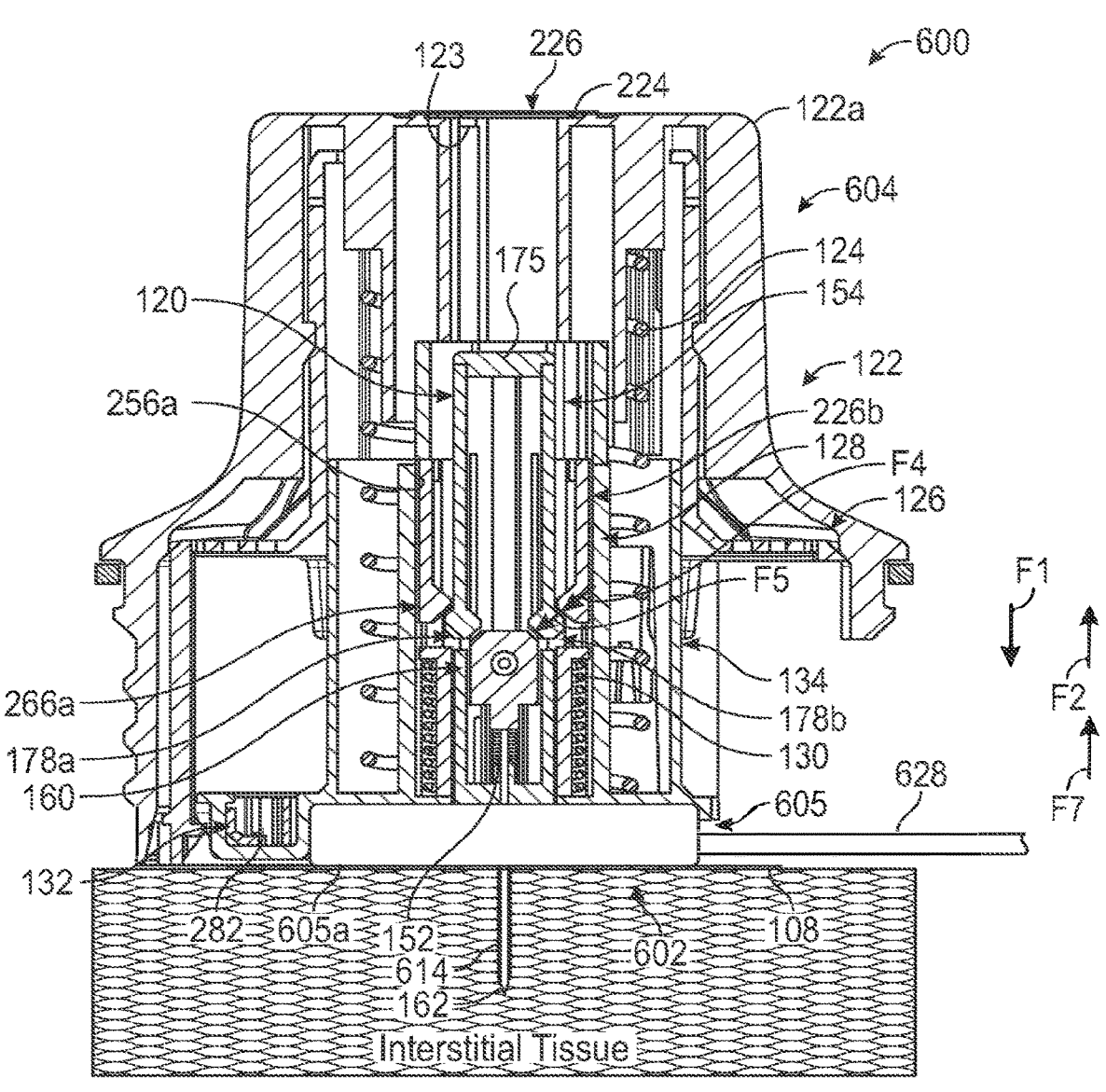
FIG. 21 is a cross-section view of another exemplary disposable medical device introduction system, taken from the perspective of line 2-2 of FIG. 1, which illustrates a disposable inserter in a second position and the insertion needle associated with the needle cartridge of the disposable inserter in the first, extended state for deploying an infusion unit onto an anatomy.

It should be noted that while the disposable medical device introduction system 100 is described herein as being used to deploy the physiological characteristic sensor assembly 102, including the physiological characteristic sensor 106, on the anatomy, a disposable medical device introduction system may be configured differently. In this regard, with reference to FIG. 21, a disposable medical device introduction system 600 is shown. As the disposable medical device introduction system 600 includes the same or similar components as the disposable medical device introduction system 100 discussed with regard to FIGS. 1-17, the same reference numerals will be used. In this example, the disposable medical device introduction system 600 includes an infusion unit 602 and a disposable inserter 604. In FIG. 21, the disposable inserter 604 is shown in the second position, in which the disposable inserter 604 is coupling the infusion unit 602 to the anatomy.

The infusion unit 602 may comprise any suitable infusion unit associated with an infusion set for dispensing a fluid to a user for use with the disposable inserter 604, and thus, the infusion unit 602 will not be discussed in great detail herein. Generally, the infusion unit 602 and the disposable inserter 604 may be packaged together for use by a consumer or user. The infusion unit 602 defines a fluid flow path from a fluid infusion device, such as an insulin pump, to a body of a user. In this example, with reference to FIG. 22, the infusion unit 602 includes a hub 605 and the adhesive patch 108.

Briefly, the hub 605 includes an inlet 610, a conduit 612 and a cannula 614 (FIG. 21). The hub 605 may also define a bore 616, which enables the insertion needle 162 to pass through to insert the cannula 614 into the anatomy. The bore 616 may be covered by a septum. The inlet 610 fluidly couples the hub 605 to a tubing 628 to define a fluid flow path between the infusion unit 602 and the fluid infusion device. Generally, the hub 605 is composed of a biocompatible polymer, and may be cast, printed, molded, etc. The inlet 610, the conduit 612 and the bore 616 may each be integrally formed with the hub 605, and the cannula 614 may comprise a portion of flexible tubing, which is formed discretely and coupled to the hub 605 via ultrasonic welding, for example. In certain embodiments, the tubing 628 may extend through the inlet 610 and the conduit 612 and exit through the bore 616 to define the cannula 614.

The inlet 610 is defined through a perimeter or circumference of the hub 605 and is in fluid communication with the conduit 612. The inlet 610 is fluidly coupled to the tubing 628, which is a source of fluid for the infusion unit 602. Generally, the tubing 628 is fluidly coupled to the fluid reservoir of the fluid infusion device, such as an infusion pump, to receive a fluid, such as insulin. The conduit 612 extends radially from the inlet 610 to the bore 616. The conduit 612 defines a fluid flow path from the inlet 610 to the bore 616. The bore 616 is defined axially though the hub 605. The bore 616 enables the insertion needle 162 to pass through the hub 605 to couple the cannula 614 to the anatomy, and also defines a fluid flow path between the conduit 612 and the cannula 614. The cannula 614 extends axially along a central axis defined by the bore 616 (FIG. 21). The cannula 614 defines a fluid flow path from the infusion unit 602 to the anatomy (FIG. 21). The adhesive patch 108 is coupled to the hub 605 along a bottom surface 605*a* (FIG. 21) of the hub 605.

With reference back to FIG. 21, in various embodiments, the infusion unit 602 is coupled to the disposable inserter 604 for shipping and delivering the infusion unit 602 to the user. The disposable inserter 604 is manipulatable by a user to couple the cannula 614 and the infusion unit 602 to the user. The disposable inserter 604 includes the needle cartridge 120, the plunger 122, the insertion spring 124, the frame 126, the retractor 128, the retraction spring 130, the retainer 132 and the carrier 134. In this example, the disposable inserter 604 is substantially the same as the disposable inserter 104, however, the disposable inserter 604 does not include the magnet 136 or the cap 138, and a portion of the plunger 122, the frame 126, the carrier 134 and the retainer 132 are removed to accommodate the tubing 628 that extends from the hub 605. It should be noted that the plunger 122, the frame 126, the carrier 134 and the retainer 133 may be modified differently to accommodate the tubing 628 coupled to the infusion unit 602. Generally, the plunger 122, the frame 126, the carrier 134 and the retainer 133 need material removed to accommodate the tubing 628 with a predetermined amount of clearance about the tubing 628. As the components of the disposable inserter 604 are substantially the same as the components of the disposable inserter 104 except for the removal of the portion of the plunger 122, the frame 126, the carrier 134 and the retainer 132 to accommodate the tubing 628, the disposable inserter 604 will not be discussed in great detail herein.

It should be noted that in certain examples, a pedestal or over covering may surround the cannula 614 and the insertion needle 162 during shipping to inhibit accidental contact with the insertion needle 162 and/or cannula 614. Also, it should be noted that while the disposable inserter 604 is described herein as not including the cap 138, in certain embodiments, the disposable inserter 604 may include a cap, similar to cap 138, that presses onto the plunger 122. In this example, the cap may include a projection, similar to the projection 310, to support the infusion unit 602 during shipping to the user. The press-on cap also includes clearance for the tubing 628, and may include a notch or other clearance formed about a perimeter of the cap to accommodate the tubing 628.

Generally, the hub 605 is coupled to the carrier 134 and retained by the retainer 132. The disposable inserter 604, including the hub 605, may be sterilized in suitable packaging and shipped to an end user. Once received, the user may remove the disposable inserter 604 from the packaging to expose the hub 608 for insertion. The user may position the disposable inserter 604 at the desired insertion site, which may or may not be visible to the user. The user may depress the plunger 122, which releases the carrier 134 and the retainer arms 282 of the retainer 132. The release of the carrier 134 and the retainer arms 282 separates the hub 605 from the disposable inserter 604. Once the carrier 134 is released from the frame 126, the insertion spring 124 applies the force F1 to couple the hub 605 to the user. The insertion needle 162 is maintained in the first, extended state during the deployment of the hub 605 onto the anatomy due to the forces F4, F5 applied to the needle carrier 160 by the lock arms 178*a*, 178*b* and the retaining arms 266*a*, 266*b*, respectively.

Generally, once the insertion spring 124 deploys the carrier 134 and the hub 605 is coupled to the anatomy, the retraction spring 130 applies the force F2 and retracts the retractor 128 upward toward the access opening 224. Once the retraction spring 130 has moved the retractor 128 past the sidewall 256*a* of the carrier 134, the force F7 of the third spring 152 is greater than a force applied by the retaining arms 266*a*, 266*b* and the lock arms 178*a*, 178*b*, as the retaining arms 266*a*, 266*b* and the lock arms 178*a*, 178*b* are able to expand outwardly or deflect unrestrained by the carrier 134. The force F7 applied as the third spring 152 expands moves the needle carrier 160, along with the insertion needle 162, toward the cap 175 of the cartridge housing 154, thereby moving the insertion needle 162 to the second, retracted state (FIG. 15). In the second, retracted state, the insertion needle 162 is fully contained within the cartridge housing 154.

Figures 22, 23:
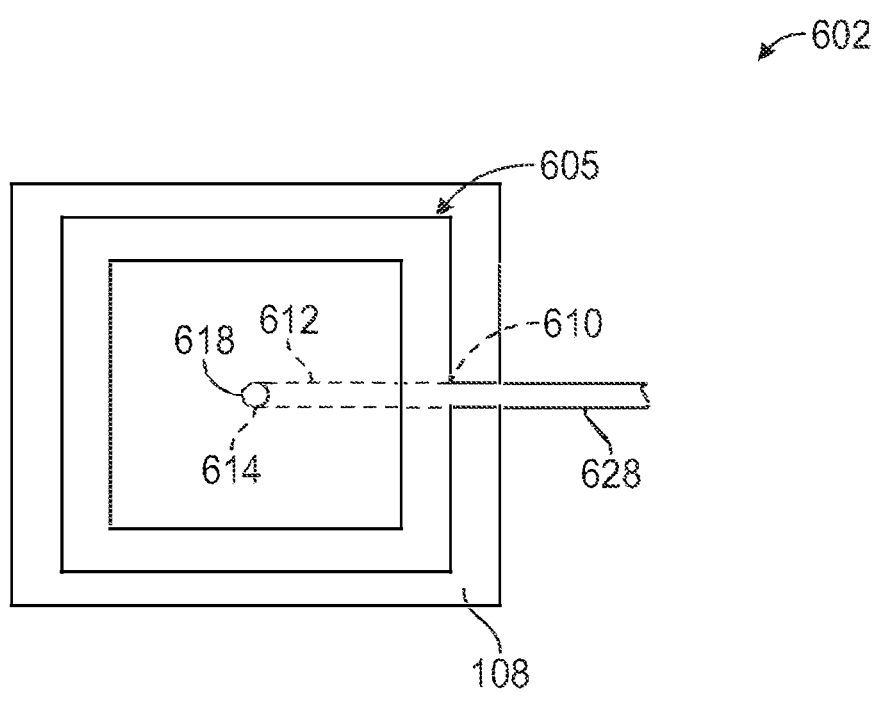
FIG. 22 is a top view of the infusion unit for use with the disposable inserter of FIG. 21 in accordance with various embodiments.
FIG. 23 is a schematic illustration of the infusion unit deployed on the anatomy to define a fluid flow path to a user.

The continued application of the force F2 of the retraction spring 130 moves the retractor 128, and thus, the needle cartridge 120 toward the first end 122*a* of the plunger 122. The access cover 226 is removed, and the retraction spring 130 is able to fully expand, to move the retractor 128 toward the first end 122*a* of the plunger 122 to seat the retractor 128 against the surface 123 (as shown in FIG. 17). With the retraction spring 130 fully expanded, the cap 175 and the first cartridge end 176 extend beyond the surface 122*c* of the plunger 122 at the first end 122*a*, which enables the user to easily grasp and remove the needle cartridge 120 from the disposable inserter 604. With reference to FIG. 23, with the infusion unit 602 coupled to the anatomy by the disposable inserter 604, the tubing 628 defines a fluid flow path to the anatomy of the user via the cannula 614. The fluid flow path through the tubing 628 is fluidly coupled to the cannula 614 of the hub 605 via the conduit 612. The tubing 628 may be fluidly coupled to the fluid reservoir of the fluid infusion device, such as an insulin reservoir of an insulin pump.

Thus, the disposable inserter 104, 404, 604, which includes the needle cartridge 120, enables the disposable inserter 104, 404, 604 to be recycled or otherwise disposed of easily by the user, without requiring disposal in a biohazard and/or sharps container. In this regard, the use of the needle cartridge 120 to contain the insertion needle 162 after insertion of the glucose sensor 114 or cannula 414, 614, respectively, enables the biohazard (the insertion needle 162) to be removed from the disposable inserter 104, 404, 604 for separate disposal, thereby enabling recycling of the disposable inserter 104, 404, 604. The recycling of the disposable inserter 104, 404, 604 is environmentally friendly. Moreover, the easy disposal of the disposable inserter 104, 404, 604 improves convenience for the user. In addition, the user may easily dispose of the needle cartridge 120 once removed from the disposable inserter 104, 404, 604.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In addition, certain terminology may also be used in the following description for the purpose of reference only, and thus are not intended to be limiting. For example, terms such as "upper", "lower", "above", and "below" refer to directions in the drawings to which reference is made. Terms such as "front", "back", "rear", "side", "outboard", and "inboard" describe the orientation and/or location of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second", and other such numerical terms referring to structures do not imply a sequence or order unless clearly indicated by the context.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

I claim:

1. A disposable inserter for a medical device, comprising:
a carrier to receive the medical device, the carrier comprising at least one annular projection;
a retractor received within the at least one annular projection and movable relative to the at least one annular projection, the retractor having at least one retaining arm;
a needle cartridge slidably coupled to the retractor that includes an insertion needle, and the at least one retaining arm engages the needle cartridge to maintain the insertion needle in a first, extended state, and a movement of the retractor relative to the at least one annular projection releases the at least one retaining arm to move the insertion needle from the first, extended state to a second, retracted state; and
a plunger that defines an access opening, wherein the needle cartridge is removable through the access opening.

2. The disposable inserter of claim 1, wherein the needle cartridge includes a cartridge housing that contains the insertion needle, and at least one lock arm is defined on the cartridge housing that cooperates with the at least one retaining arm to maintain the insertion needle in the first, extended state.

3. The disposable inserter of claim 2, wherein the needle cartridge includes a needle carrier coupled to the insertion needle, and the at least one lock arm is configured to apply a force to the needle cartridge to maintain the insertion needle in the first, extended state.

4. The disposable inserter of claim 3, wherein the needle carrier includes at least one contact surface, and the at least one lock arm includes a lock arm end with at least one first contact surface to apply the force to the at least one contact surface.

5. The disposable inserter of claim 4, wherein the lock arm end of the at least one lock arm includes a second contact surface opposed from the at least one first contact surface, and the second contact surface is configured to contact a retaining arm end of the at least one retaining arm to maintain the insertion needle in the first, extended state.

6. The disposable inserter of claim 3, wherein the needle cartridge further comprises a biasing member positioned between the needle carrier and an end of the cartridge housing, and in the first, extended state, the biasing member is compressed by the needle carrier.

7. The disposable inserter of claim 6, wherein the movement of the retractor relative to the at least one annular projection releases the at least one lock arm to release the needle carrier to move the insertion needle to the second, retracted state by the biasing member.

8. The disposable inserter of claim 1, wherein the retractor includes at least one internal slot and the needle cartridge includes a cartridge housing having at least one coupling tab that is slidably coupled to the at least one internal slot.

9. The disposable inserter of claim 1, wherein the plunger includes an access cover removably coupled to the access opening.

10. The disposable inserter of claim 1, wherein the movement of the retractor relative to the at least one annular projection urges the needle cartridge toward the access opening.

11. A disposable medical device introduction system, comprising:

a medical device; and a disposable inserter, including:

a plunger defining an access opening enclosed by a removable access cover;

a carrier to receive the medical device, the carrier comprising a projection, wherein the carrier is movable relative to the plunger;

a retractor movable relative to the projection, the retractor having at least one retaining element; and a needle cartridge slidably coupled to the retractor and comprising an insertion needle, and the at least one retaining element engages the needle cartridge to maintain the insertion needle in a first, extended state and a movement of the retractor relative to the projection releases the at least one retaining element to move the insertion needle from the first, extended state to a second, retracted state, and the needle cartridge is removable through the access opening.

12. The disposable medical device introduction system of claim 11, wherein the needle cartridge includes a cartridge housing that contains the insertion needle, and at least one lock arm is defined on the cartridge housing, wherein the at least one lock arm cooperates with the at least one retaining element to maintain the insertion needle in the first, extended state.

13. The disposable medical device introduction system of claim 12, wherein the needle cartridge includes a needle carrier coupled to the insertion needle, and the at least one lock arm is configured to apply a force to the needle cartridge to maintain the insertion needle in the first, extended state.

14. The disposable medical device introduction system of claim 13, wherein the needle cartridge further comprises a biasing member positioned between the needle carrier and an end of the cartridge housing, and in the first, extended state, the biasing member is compressed by the needle carrier.

15. The disposable medical device introduction system of claim 14, wherein the movement of the retractor relative to the at least one annular projection releases the at least one lock arm to release the needle carrier to move the insertion needle to the second, retracted state by the biasing member.

16. The disposable medical device introduction system of claim 11, wherein in the second, retracted state, the insertion needle is retained wholly within a rest of the needle cartridge.

17. The disposable medical device introduction system of claim 11, wherein the retractor includes at least one internal slot and the needle cartridge includes a cartridge housing having at least one coupling tab that is slidably coupled to the at least one internal slot.

18. The disposable medical device introduction system of claim 11, wherein the movement of the retractor relative to the at least one annular projection urges the needle cartridge toward the access opening.

19. The disposable medical device introduction system of claim 11, wherein the medical device is a physiological characteristic sensor, an infusion hub or an infusion unit.

20. A disposable inserter for a medical device, comprising:

a carrier configured to receive the medical device;

a retractor movable relative to the carrier;

a needle cartridge slidably coupled to the retractor that includes an insertion needle, wherein the retractor engages the needle cartridge to maintain the insertion needle in a first, extended state, and wherein a movement of the retractor relative to the carrier releases the retractor to move the insertion needle from the first, extended state to a second, retracted state; and a plunger that defines an access opening, wherein the needle cartridge is removable through the access opening.

\* \* \* \* \*